(12) United States Patent
Bok et al.

(10) Patent No.: US 7,223,793 B2
(45) Date of Patent: May 29, 2007

(54) PHENOLIC ACID DERIVATIVES AND COMPOSITION FOR PREVENTING OR TREATING BLOOD LIPID LEVEL-RELATED DISEASES COMPRISING THE SAME

(75) Inventors: Songhae Bok, Taejon (KR); Sangku Lee, Taejon (KR); Taesook Jeong, Taejon (KR); Euneai Kim, Taejon (KR); Surksik Moon, Taejon (KR); Myungsook Choi, Taegu (KR); Byunghwa Hyun, Taejon (KR); Chulho Lee, Taejon (KR); Yangkyu Choi, Taejon (KR); Gootaeg Oh, Taejon (KR)

(73) Assignee: Bionutrigen Co., Ltd., Taejon (KR)

( * ) Notice: Subject to any disclaimer, the term of this patent is extended or adjusted under 35 U.S.C. 154(b) by 400 days.

(21) Appl. No.: 10/309,099

(22) Filed: Dec. 4, 2002

(65) Prior Publication Data
US 2003/0199566 A1    Oct. 23, 2003

(30) Foreign Application Priority Data
Dec. 14, 2001  (KR)  .............................. 2001-79485

(51) Int. Cl.
A61K 31/216   (2006.01)
A61K 31/24    (2006.01)
C07C 229/36   (2006.01)
(52) U.S. Cl. .................. 514/513; 514/539; 560/39
(58) Field of Classification Search ................ 560/39; 514/513, 529, 539
See application file for complete search history.

(56) References Cited

U.S. PATENT DOCUMENTS
4,602,027 A * 7/1986 Meguro et al. ............. 514/374

FOREIGN PATENT DOCUMENTS
KR   2000-0023161    4/2000
KR   2001-0017959    3/2001
WO   WO 02/16331 A1 *  2/2002

OTHER PUBLICATIONS

Nash, DT, American Journal of Cardiology, 78 (6A), 1996, pp. 26-31.*

Keller et al., Phytochemistry, vol. 42, No. 2, pp. 389-396, (1996).*
Zhao et al., European Journal of Medicinal Chemistry (1993), 28(12), 949-54.*
Mock et al., Phytochemistry, vol. 34, No. 1, pp. 157-159 (1993).*
Bokern et al., Phytochemistry, vol. 30, No. 10, pp. 3261-6265 (1991).*
Van Sumere et al., Journal of Chromatography, 234, (1982), 141-155.*
Meguro et al, Chemistry & Pharmaceutical Gulletin (1986), 34(7), pp. 2840-2851.*
Trennheuser et al., Phytochemistry, vol. 37, No. 3, pp. 899-903, (1994).*
Bokern et al., Planta (1991), 184, pp. 261-270.*
Berlin et al., Journal of Natural Products (1982), 45(1), 88-93.*
Conde et al., European Journal of Organic Chemistry (1999), (11), 2835-2839.*
Filipp Imperato, Chemistry & Industry, vol. 9., p. 388, (1980).*
Database CAS Online on STN, Chem. Abstr., Accession No. 1990:513236, Duran et al., Progress in Clinical and Biological Research (1990), vol. 321, pp. 419-426, abstract.*
Database CAS Online on STN, Chem. Abstr., Accession No. 2001:729677, DE 20110355 U1 (Wella Ag, Germany), Oct. 4, 2001, (Oct. 4, 2004), abstract.*
Jungblut et al., Acta Horticulturae 381, 1994, pp. 470-473.*
Kwon, Byoung-Mog et al. "Synthesis and In Vitro Cytotoxicity of Cinnamaldehydes to Human Solid Tumor Cells." *Archives of Pharmacal Research*. vol. 21, No. 2. pp. 147-152, 1998.
Kwon, Byoung-Mog et al. "2'—Hydroxycinnamaldehyde from Stem Bark of *Cinnamomum cassia*." Planta Medica . vol. 62, 183-184, 1996.
Kwon, Byoung-Mog et al. "Synthesis and Biological Activity of Cinnamaldehydes as Angiogenesis Inhibitors." *Bioorganic & Medicinal* Chemistry Letters. vol. 7, No. 19. pp. 2473-2476, 1997.

* cited by examiner

*Primary Examiner*—Rebecca Anderson
(74) *Attorney, Agent, or Firm*—The Nath Law Group; Gary M. Nath; Susanne M. Hopkins

(57) ABSTRACT

The present invention relates to phenolic acid derivatives of the formula I and compositions for the preventing and the treating blood lipid level-related diseases comprising the phenolic acid derivatives. The compounds have excellent effects of reducing blood lipid level, inhibiting cholesterol metabolism-related enzymes and preventing and treating blood lipid level-related diseases.

6 Claims, 8 Drawing Sheets artery of control group
(stained with H&E, x100)

artery of lovastatin group
(stained with H&E, x100)

artery of BN30028 group
(stained with H&E, x100)

liver tissue of control group
(stained with H&E, x100)

liver tissue of lovastatin group
(stained with H&E, x100)

liver tissue of BN30028 group
(stained with H&E, x100)

PHENOLIC ACID DERIVATIVES AND COMPOSITION FOR PREVENTING OR TREATING BLOOD LIPID LEVEL-RELATED DISEASES COMPRISING THE SAME

BACKGROUND OF THE INVENTION

1. Field of the Invention

The present invention relates to compositions for preventing and treating blood lipid level-related diseases comprising phenolic acid derivatives.

2. Description of the Related Art

Currently, coronary cardiovascular disease accounts for more than 30% of the total causes of death and become serious problems in advanced countries such as United States, Europe, etc. Also, heart diseases are tending to increase in developing countries due to westernization of dietary life, lack of exercise, etc. It is known that when the plasma cholesterol level is high, fat along with macrophages, foam cells, etc. is deposited on the wall of blood vessels to form plaque, causing arteriosclerosis, which blocks blood flow (Ross, R., *Nature*, 362, 801-809(1993)).

It has been reported that the plasma cholesterol level can be reduced by suppressing absorption of cholesterol. Acyl CoA-cholesterol-O-acyltransferase (ACAT) is an enzyme that converts cholesterol into cholesterol ester in the tissue of the human body. In experimental and clinical arteriosclerosis phenomenon, the formation of foam cells derived from macrophages or smooth muscle cells is a very important factor. The foam cells are formed by the action of ACAT and contain plenty of cholesterol ester transferred by LDL in the blood. Since the foam cells are frequently found on the wall of artery as the activity of ACAT increases, it is highly possible for ACAT inhibitor to act as an agent for preventing arteriosclerosis. Also, if the ACAT activity in the liver is suppressed, LDL-cholesterol level in the circulating blood may be lowered (Witiak, D. T. and D. R. Feller(eds), *Antilipidemic Drugs: Medicinal, Chemical, and Biochemical Aspects*, Elsevier, pp159-195(1991)).

Further, it has been reported that the plasma cholesterol level can be reduced by inhibiting the activity of cholesterol ester transfer protein (CETP) which mediates the cholesterol transfers between the lipoproteins, or 3-hydroxy-3-methylglutaryl coenzyme A (HMG-CoA) reductase which is involved in the biosynthesis of cholesterol in the liver. HMG-CoA reductase mediates the synthesis of mevalonic acid, an intermediate in the biosynthesis of sterols or isoprenoids. Thus, the inhibition of this enzyme leads to the reduction of the rate of cholesterol biosynthesis, by which hypercholesterolemia can be effectively treated (William, W. P., *Cardiovascular Pharmacology*, Kanu Chatterjee(ed), Wolfe Pullishing, 8.6-8.7 (1994)). HMG-CoA reductase inhibitors commonly used are those derived from *Penicillium* sp. and *Aspergillus* sp., including Lovastatin™ and Simvastatin™ developed by Merck Co. (U.S.A.) and Pravastatin™ developed by Sankyo Co. (Japan). However, statins are known to induce an adverse side effect to the central nervous system (Saheki, A. T. et al., *Pharm. Res.*, 11, 304-311 (1994)). Further, although Lovastatin and Simvastatin may reduce the plasma LDL cholesterol level by enhancing the activity of LDL receptor in the liver, they cause side effects such as increase in diverse enzymes including creatine kinase and rhabdomyolysis (Farmer, J. A. et al., *Baillers-clin. Endocrinol. Metab.*, 9, 825-847 (1995)).

Meanwhile, the function of the liver is deteriorated by the excessive intake of fat-containing foods or alcohol, and infection of hepatitis B or C virus. Such conditions may develop into hepatitis, hepatic cirrhosis, liver cancer, etc. Particularly, the excessive intake of fat and alcohol through foods causes fatty liver wherein a large amount of lipids is deposited in the liver tissue and the levels of serum GOT (glutamate-oxaloacetate transaminase), GPT (glutamate-pyruvate transaminase) and γ GTP (γ-glutamyl transpeptidase) are elevated (T. Banciu, et al., *Med. Interne.*, 20, 69-71(1982); and A. Par, et al., *Acta. Med. Acad. Sci. Hung.*, 33, 309-319(1976)).

It has been reported by Hayashi et al. that an extract from green tea improved liver functions in a rat by preventing the elevation of serum GOT and GPT (M. Hayashi, et al., *Nippon Yakuri gaku Zasshi*, 100, 391-399(1992)).

The present inventors already discovered that bioflavonoids such as hesperidin, hesperetin, naringin and naringenin, and extracts of pericarp of citrus fruit abundantly containing the foregoings significantly reduce the plasma cholesterol level, inhibit the activity of ACAT, strongly inhibit the formation or accumulation of macrophage-lipid complex on the endothelial wall of an artery and have therapeutic and prophylactic effects of hepatic disease and filed applications for patent based on these discoveries (WO98/16220, WO098/16221, Korean Patent Application Nos. 98-10888 and 98-10889).

The present inventors also have studied phenolic acid derivatives, which is employed as a precursor in the biosynthesis of bioflavonoids and forms a backbone structure of bioflavonoids (W. Heller and G. Forkman, Biosynthesis of flavonoids, In the Flavonoids-Advanced in Research.(ed) J. B. Harborne, Chapman & Hall Co., London, 1993. pp 500-535), for the functions of the previous compounds. As a result it has been discovered that it can reduce plasma cholesterol level, inhibit the accumulation of macrophage-lipid complex on the arterial endothelium and prevent damage of liver cells and fatty liver and on the basis of this discovery, the present invention has been completed.

SUMMARY OF THE INVENTION

It is an object of the present invention to provide phenolic acid derivatives with excellent effect of reducing plasma lipid level.

It is a further object of the present invention to provide a method for producing phenolic acid derivatives with excellent effect of reducing plasma lipid level.

It is another object of the present invention to provide an agent for preventing and treating blood lipid level-related diseases comprising phenolic acid derivatives with excellent effect of reducing plasma lipid level.

It is yet another object of the present invention to provide a composition for inhibiting cholesterol metabolism-related enzymes comprising phenolic acid derivatives with excellent effect of reducing plasma lipid level.

In accordance with one aspect of the present invention, there is provided a phenolic acid derivative of the formula I:

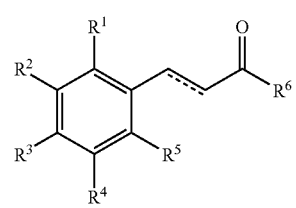

I wherein,
R¹, R², R³, R⁴ and R⁵ are independently hydrogen, hydroxy or $C_1$-$C_6$ alkoxy;
R⁶ is

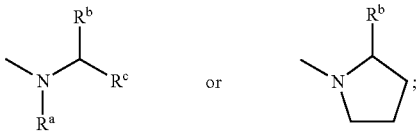

R$^a$ is hydrogen or acetyl;
R$^b$ is COOR$^d$ or $CH_2OR^d$;
R$^c$ is hydrogen, benzyl, hydroxybenzyl, imidazolemethyl, indolemethyl, linear or branched $C_1$-$C_6$ alkyl, or $C_1$-$C_6$ alkyl substittuted with hydroxy, thiol(SH), thiomethyl ($SCH_3$), NHR$^d$, $CNHNH_2$, $CONH_2$ or COOR$^d$; and
R$^d$ is hydrogen, methyl, ethyl or benzyl.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF PREFERRED EMBODIMENTS

Figure 1A:
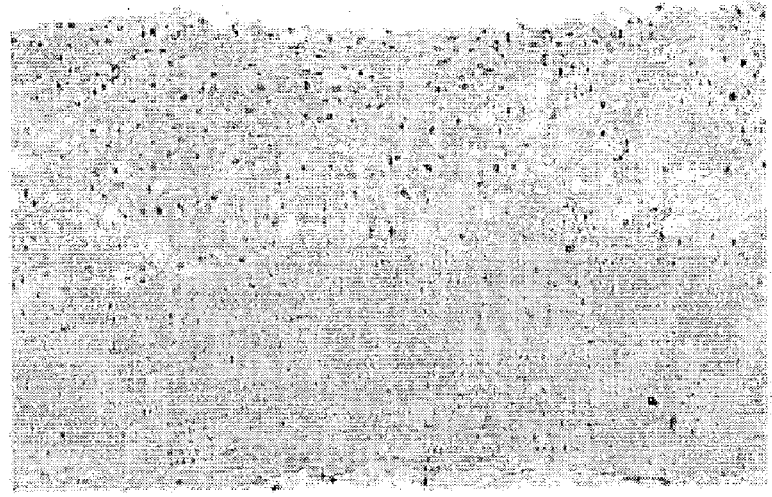
FIGS. 1a, 1b and 1c are photographs taken of the arterial endothelium of the control rabbit, and rabbits administered with lovastatin and BN30028, respectively.

The present invention is directed to a phenolic acid derivative of the formula I:

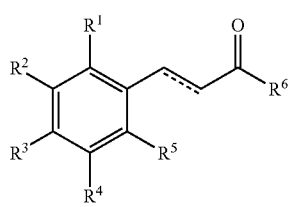

I wherein,
R¹, R², R³, R⁴ and R⁵ are independently hydrogen, hydroxy or $C_1$-$C_6$ alkoxy;

R⁶ is

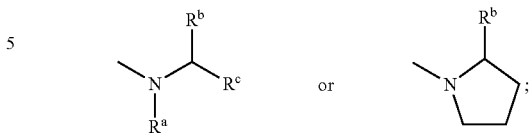

R$^a$ is hydrogen or acetyl;
R$^b$ is COOR$^d$ or $CH_2OR^d$;
R$^c$ is hydrogen, benzyl, hydroxybenzyl, imidazolemethyl, indolemethyl, linear or branched $C_1$-$C_6$ alkyl, or $C_1$-$C_6$ alkyl substittuted with hydroxy, thiol(SH), thiomethyl ($SCH_3$), NHR$^d$, $CNHNH_2$, $CONH_2$ or COOR$^d$; and
R$^d$ is hydrogen, methyl, ethyl or benzyl.

Preferable compounds of the formula I include the compounds wherein R¹, R², R³, R⁴, R⁵ are independently hydrogen, hydroxy, methoxy or ethoxy; R$^a$ is hydrogen or acetyl; R$^b$ is COOH; and R$^c$ is hydrogen, benzyl, hydroxybenzyl, imidazolemethyl, indolemethyl, linear or branched $C_1$-$C_6$ alkyl, or $C_1$-$C_6$ alkyl substituted with hydroxy, thiomethyl ($SCH_3$), $NH_2$, $CNHNH_2$, $CONH_2$ or COOH.

More preferable compounds of the formula I include
2-[3-(4-hydroxyphenyl)propionylamino]-3-indolyl propionic acid methyl ester;
2-[3-(3,4-dihydroxyphenyl)acryloylamino]-3-indolyl propionic acid ethyl ester;
2-[3-(3,4-dihydroxyphenyl)propionylamino]-3-indolyl propionic acid ethyl ester;
2-[3-(3,4-dihydroxyphenyl)acryloylamino]-3-phenyl propionic acid methyl ester;
2-[3-(3,4-dihydroxyphenyl)propionylamino]-3-phenyl propionic acid methyl ester;
2-[3-(4-hydroxyphenyl)acryloylamino]-3-phenyl propionic acid methyl ester;
2-[3-(4-hydroxyphenyl)propionylamino]-3-phenyl propionic acid methyl ester;
4-carbamoyl-2-[3-(3,4-dihydroxyphenyl)propionylamino] butyric acid ethyl ester;
4-carbamoyl-2-[3-(3,4-dihydroxyphenyl)propionylamino] butyric acid;
2-[3-(3,4-dihydroxyphenyl)propionylamino] pentanedioic acid diethyl ester;
2-[3-(3,4-dihydroxyphenyl)propionylamino] pentanedioic acid;
2-[3-(3,4-dihydroxyphenyl)propionylamino]-4-methylsulfanyl butyric acid;
2-[3-(3,4-dihydroxyphenyl)propionylamino] propionic acid;
2-[3-(3,4-dihydroxyphenyl)propionylamino] acetic acid;
2-[3-(3,4-dihydroxyphenyl)propionylamino]-3-methyl butyric acid;
2-[3-(3,4-dihydroxyphenyl)propionylamino]-3-pyrrolyl propionic acid;
2-[3-(3,4-dihydroxyphenyl)propionylamino]-3-(4-hydroxyphenyl) propionic acid;
2-[3-(3,4-dihydroxyphenyl)propionylamino]-3-hydroxy propionic acid;
6-amino-2-[3-(3,4-dihydroxyphenyl)propionylamino] hexanoic acid;
2-[3-(3,4-dihydroxyphenyl)propionylamino] succinic acid;
2-[3-(3,4-dihydroxyphenyl)propionylamino]-3-hydroxy butyric acid;
2-[3-(3,4-dihydroxyphenyl)propionylamino]-3-methyl pentanoic acid;

2-[3-(4-hydroxyphenyl)propionylamino]pentanedioic acid diethyl ester;

2-[3-(4-hydroxyphenyl)propionylamino]-4-methyl sulfanyl butyric acid methyl ester;

2-[3-(4-hydroxyphenyl)propionylamino]acetic acid ethyl ester;

2-[3-(4-hydroxyphenyl)propionylamino]-3-methyl butyric acid methyl ester;

2-[3-(4-hydroxyphenyl)propionylamino]-3-phenyl propionic acid; and

2-[3-(4-hydroxyphenyl)propionylamino]-3-methyl butyric acid.

The compounds of the formula I can be prepared by the following method. That is, phenyl propionic acid or cinnamic acid substituted with a member selected from the group consisting of hydrogen, hydroxy and $C_1$-$C_6$ alkoxy, and amino acid ester or amino alcohol are dissolved in an organic solvent along with an additive such as 1-hydroxybenzotriazole, 1-hydroxy-7-azabenzotriazole or N-hydroxysuccinimide. Tertiary amine base is added to the resulting solution at 0 to 25° C. and then stirred for 1 to 30 minutes. Then, carbodiimide as a condensing agent is added and stirred for 10 hours to one day at room temperature.

Examples of the above-mentioned substituted phenyl propionic acid include 3,4-dihydroxyphenyl propionic acid, 3-(4-hydroxyphenyl)propionic acid and the like and examples of the substituted cinnamic acid include 4-hydroxycinnamic acid, 4-hydroxyhydrocinnamic acid, 2-hydroxycinnamic acid, 2-hydroxyhydrocinnamic acid, 3-hydroxycinnamic acid, 3-hydroxyhydrocinnamic acid, 3,4-dihydroxycinnamic acid, 3,4-dihydroxyhydrocinnamic acid, 4-hydroxy-3-methoxycinnamic acid, 4-hydroxy-3-methoxyhydrocinnamic acid, 3-hydroxy-4-methoxycinnamic acid, 3-hydroxy-4-methoxyhydrocinnamic acid and the like. Examples of the additive include 1-hydroxybenzotriazole, 1-hydroxy-7-azabenzotriazole or N-hydroxysuccinimide. Examples of the organic solvent include dimethylformamide (DMF), dimethylsulfoxide (DMSO), tetrahydrofuran(THF) or mixtures thereof. Examples of the tertiary amine base include triethylamine, diisopropylethylamine, pyridine or 4-dimethylaminopyridine. Further, as a condensing agent, carbodiimides such as 1,3-dicyclohexylcarbodiimide, 1-[3-(dimethylamino)propyl]-3-ethylcarbodiimide hydrochloride or 1-cyclohexyl-3-(2-morphorinoethyl)carbodiimide metho-4-toluensulfonate and the like can be used. In addition, as the amino acid ester, methyl ester, ethyl ester or benzyl ester of alanine, arginine, asparagine, aspartic acid, cysteine, cystine, glutamic acid, histidine, isoleusine, leusine, lysine, methionine, phenylalanine, proline, serine, threonine, tryptophan or valine can be used. The aminoalcohol can be prepared by dissolving an amino acid ester in ethylether or tetrahydrofuran (THF) and mixing with lithium aluminium hydride to convert an ester group into an alcohol group, followed by stirring for 1 to 12 hours, preferably 5 to 6 hours at room temperature for alkylation.

The resulting solution is diluted in water and extracted with ethyl acetate (EtOAc). The extract is washed with salt water, filtered and concentrated to form a product in an ester form. The compounds of the present invention can be purified by chromatography such as silica gel chromatography or C-18 HPLC.

Also, the carboxylic acid type derivative of the formula I wherein $R^b$ is COOH can be prepared by hydrolysis of the product in an ester form, prepared as above, under a basic condition. Here, as a base, lithium hydroxide, sodium hydroxide or potassium hydroxide can be used. As a solvent for reaction, water or a mixture of water and tetrahydrofuran, 1,4-dioxane, methylalcohol, ethylalcohol in a ratio of 1:1 to 1:10 can be used. The reaction temperature is in the range of room temperature to a boiling point of the solvent. After completion of the reaction for 2 to 24 hours, the reaction is neutralized with aqueous hydrochloric acid, extracted with EtOAc, dried, filtered and concentrated to from a derivative in an ester form.

A compound of the formula I wherein $R^b$ is $CH_2OR^d$ can be prepared by reducing the ester compound of the formula I wherein $R^b$ is $CH_2OR^d$ with a reducing agent to reduce $R^b$ in an alcohol group of $CH_2OH$, followed by alkylation.

The phenolic acid derivatives of the present invention have excellent effect on reducing plasma cholesterol and neutral fat level and thus are expected to be useful in the prevention and treatment of blood lipid level-related diseases. In the present invention, the term of "blood lipid level-related disease" means a disease which is caused by a high level of blood lipid, including for example, hyperlipidemia, hypercholesterolemia, arteriosclerosis, fatty liver and the like. Also, the compounds of the present invention shows superior effects of inhibiting enzymes, such as ACAT, which are involved in lipid metabolism and protecting functions of the liver. It was shown in an experimental using a mouse that the compounds of the present invention do not have any toxicity or mitogenicity.

Therefore, the present invention provides a pharmaceutical composition for reducing blood lipid level, inhibiting cholesterol metabolism-related enzymes, treating or preventing elevated blood lipid level-related diseases, or protecting liver functions, which comprises a phenolic acid derivative of the formula I as an active ingredient with a pharmaceutically acceptable excipients, carriers or diluents.

A pharmaceutical formulation may be prepared using the composition of the present invention in accordance with any of the conventional procedures. The formulation may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxy-benzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical composition of the present invention can be administered via various routes including oral, transdermal, subcutaneous, intravenous and intramuscular introduction. In case of human, a typical daily dose of the compound of the formula I may be between about 0.01 to 100 mg/kg body weight, more preferably 0.1 to 50 mg/kg body weight, most preferably 1 to 10 mg/kg body weight and the compound can be administered in a single dose or in divided doses.

However, it should be understood that the amount of the active ingredient actually administered ought to be determined in light of various relevant factors including the condition to be treated, the selected route of administration, the age, sex and body weight of the individual patient, and the severity of the patient's symptom. Therefore, the above dose should not be intended to limit the scope of the invention in any way.

Also, the compound of the formula I can be incorporated in foods or beverages for the purpose of reducing blood lipid level, inhibiting cholesterol metabolism-related enzymes, treating or preventing elevated blood lipid level-related diseases, or protecting liver functions. The foods or beverages may include meats; juices such as a vegetable juice(for example, carrot juice and tomato juice) and a fruit juice(for example, orange juice, grape juice, pineapple juice, apple juice and banana juice); chocolates; snacks; confectionery; pizza; food products made from cereal flour such as breads, cakes, crackers, cookies, biscuits, noodles and the like; gums; dairy products such as milk, cheese, yogurt and ice creams; soups; broths; pastes, ketchup and sauces; teas; alcoholic beverages; carbonated beverages; vitamin complexes; and various health foods. Here, the content of the compound of the formula I in a food or beverage may be in the range of 0.01 to 20 wt %, preferably, from 0.1 to 10 wt %.

The following Examples are given for further illustration of the present invention. However the present invention is not limited thereto.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

EXAMPLE 1

Preparation of 2-[3-(3,4-dihydroxyphenyl)propionylamino]-3-indolyl propionic acid ethyl ester 3,4-dihydroxyphenyl propionic acid (5.8 g, 31.8 mmol), tryptophan ethyl ester (8.1 g, 34.9 mmol), 1-hydroxybenzotriazole hydrate (5.2 g, 38.5 mmol) were dissolved in dimethylformamide (60 mL). The resulting solution was then placed in a water bath at 0° C. and treated with triethylamine (14 mL), followed by stirring for 10 minutes. To the resulting mixture, 1-[3-(dimethylamino)propyl]-3-ethylcarbodiimide hydrochloride (7.3g, 38.5 mmol) was added. After removing the water bath, the mixture was stirred for 18 hours at room temperature. The reaction was diluted in water (200 mL), extracted with ethylacetate (EtOAc) (500 mL), dried over magnesium sulfate, concentrated under reduced pressure and purified by silica gel column chromatography (column size: 45 mm×150 mm, silica gel 70-230 mesh, eluent: hexane/EtOAc (1/2)) to obtain 11.6 g of the title compound. The yield was 92%. The results of analyses of the compound are as follows:

$^1$H NMR (DMSO-d6) δ 10.83 (s, 1H), 8.70 (s, 1H), 8.60 (s, 1H), 8.26 (d, J=7.6 Hz, 1H), 7.50 (d, J=7.6 Hz, 1H), 7.34 (d, J=8.0 Hz, 1H), 7.13 (d, J=1.6 Hz, 1H), 7.07 (t, J=7.6 Hz, 1H), 6.99 (t, J=7.6 Hz, 1H), 6.60 (m, 2H), 6.41 (d, J=8.0 Hz, 1H), 4.50 (m, 1H), 4.01 (q, J=6.8 Hz, 2H), 3.13 (dd, J=14.4, 6.4 Hz, 1H), 3.03 (dd, J=14.4, 8.0 Hz, 1H), 2.58 (dd, J=8.8, 6.0 Hz, 2H), 2.32 (t, J=8.8 Hz, 2H), 1.07 (t, J=6.8 Hz, 3H) ppm. $^{13}$C NMR (DMSO-d6) δ 172.7, 172.3, 145.6, 143.9, 136.7, 132.7, 127.8, 124.3, 121.6, 119.3, 119.0, 118.7, 116.3, 116.1, 112.0, 110.2, 61.0, 53.8, 37.8, 31.1, 27.8, 14.5 ppm.

EXAMPLE 2

Preparation of 2-[3-(3,4-dihydroxyphenyl)propionylamino]-3-phenyl propionic acid methyl ester (BN30028)

Following the same procedure of Example 1 except that 3,4-dihydroxyphenyl propionic acid (1.0 g, 5.5 mmol) and phenylalanine methyl ester (1.1 g ,6.1 mmol) were used, 1.7 g of the title compound was obtained. The compound was finally purified by silica gel column chromatography (column size: 25 mm×150 mm, silica gel 70-230 mesh, eluent: hexane/EtOAc (1/2)). The results of analyses of the compound are as follows:

$^1$H NMR (CDCl$_3$) δ 7.31 (m, 3H), 6.92 (dd, J=8.4, 2.4 Hz, 1H), 6.74 (d, J=8.0 Hz, 1H), 6.68 (d, J=1.6 Hz, 1H), 6.51 (dd, J=8.0, 2.0 Hz, 1H), 6.18 (d, J=7.6 Hz, 1H), 4.83 (dd, J=13.6, 6.0 Hz, 1H), 3.66 (s, 3H), 3.01 (dd, J=6.0, 2.4 Hz, 2H), 2.76 (t, J=8.0 Hz, 2H), 2.41 (m, 2H) ppm. $^{13}$CNMR (CDCl$_3$) δ 172.9, 171.9, 144.1, 142.8, 135.4, 132.4, 129.2, 129.1,128.6, 128.5, 127.1, 120.1, 115.3, 115.2, 53.2, 52.3, 38.2, 37.7, 30.7 ppm.

EXAMPLE 3

Preparation of 2-[3-(4-hydroxyphenyl)acryloylamino]-3-phenyl propionic acid methyl ester 4-hydroxy cinnamic acid (1.0 g, 6.1 mmol), phenylalanine methyl ester (1.2 g, 6.7 mmol) and 1-hydroxybenzotriazole hydrate (1.0 g, 7.4 mmol) were dissolved in dimethylformamide (25 mL). The resulting solution was then placed in a water bath at 0°0 C. and treated with triethylamine (3.5 mL), followed by stirring for 10 minutes. To the resulting mixture, 1-[3-(dimethylamino)propyl]-3-ethylcarbodiimide hydrochloride (1.4 g, 7.4 mmol) was added. After removing the water bath, the mixture was stirred for 18 hours at room temperature. The reaction was diluted in water (60 mL), extracted with ethylacetate (EtOAc) (200 mL), dried over magnesium sulfate, concentrated under reduced pressure and purified by silica gel column chromatography (column size: 25 mm×150 mm, silica gel 70-230 mesh, eluent: hexane/EtOAc (1/1)) to obtain 1.8 g of the title compound. The yield was 91%. The results of analyses of the compound are as follows:

$^1$H NMR (CDCl$_3$) δ 7.53 (d, J=15.2 Hz, 1H), 7.31 (d, J=8.8 Hz, 2H), 7.27 (m, 3H), 7.11 (m, 2H), 6.82 (d, J=8.8 Hz, 2H), 6.20 (d, J=15.2 Hz, 1H), 6.16 (s, 1H), 5.02 (dd, J=13.6, 6.0 Hz, 1H), 3.74 (s, 3H), 3.22 (dd, J=14.0, 6.0 Hz, 1H), 3.16 (dd, J=14.0, 6.0 Hz, 1H)ppm. $^{13}$CNMR(CDCl$_3$) δ 172.3, 166.2, 158.1, 142.1, 135.7, 129.7, 129.2, 128.6, 127.2, 126.7, 116.7, 115.9, 53.4; 52.4, 37.8 ppm.

EXAMPLE 4

Preparation of 2-[3-(4-hydroxyphenyl)propionylamino]-3-phenyl propionic acid methyl ester 3-(4-hydroxyphenyl)propionic acid (1.0 g, 6.0 mmol), phenylalanine methyl ester (1.2 g, 6.7 mmol) and 1-hydroxybenzotriazole hydrate (1.0 g, 7.4 mmol) were dissolved in dimethylformamide (25 mL). The resulting solution was then placed in a water bath at 0° C. and treated with triethylamine (3.5 mL), followed by stirring for 10 minutes. To the resulting mixture, 1-[3-(dimethylamino)propyl]-3-ethylcarbodiimide hydrochloride (1.4 g, 7.4 mmol) was added. After removing the water bath, the mixture was stirred for 18 hours at room temperature. The reaction was diluted in water (60 mL), extracted with ethylacetate (EtOAc) (200 mL), dried over magnesium sulfate, concentrated under reduced pressure and purified by silica gel column chromatography (column size: 25 mm×150 mm, silica gel 70-230 mesh, eluent: hexane/EtOAc (1/1)) to obtain 1.8 g of the title compound. The yield was 91%. The results of analyses of the compound are as follows:

$^1$H NMR (CDCl$_3$) δ 7.21 (m, 3H), 6.98 (d, J=8.4 Hz, 2H), 6.93 (m, 2H), 6.74 (d, J=8.4 Hz, 2H), 5.99 (d, J=7.6 Hz, 1H), 4.87 (m, 1H), 3.68 (s, 3H), 3.04 (d, J=5.6 Hz, 2H), 2.83 (m, 2H), 2.43 (m, 2H) ppm. $^{13}$C NMR (CDCl$_3$) δ 172.2, 171.9, 154.6, 135.5, 131.8, 129.3, 129.1, 128.5, 127.1, 115.4, 53.0, 52.3, 38.3, 37.7, 30.5 ppm.

EXAMPLE 5

Preparation of 2-[3-(4-hydroxyphenyl)propionylamino]-3-indolyl propionic acid methyl ester Following the same procedure of Example 4 except that 3-(4-hydroxyphenyl)propionic acid (1.0 g, 6.0 mmol) and tryptophan methyl ester (1.44 g, 6.6 mmol) were used, 2.0 g of the title compound was obtained. The compound was finally purified by silica gel column chromatography (column size: 25 mm×150 mm, silica gel 70-230 mesh, eluent: hexane/EtOAc (1/1)). The results of analyses of the compound are as follows:

$^1$H NMR (CDCl$_3$) δ 8.48 (s, 1H), 7.40 (s, 1H), 7.39 (d, J=8.0 Hz, 1H), 7.24 (d, J=8.0 Hz, 1H), 7.11 (t, J=7.6 Hz, 1H), 7.03 (t, J=7.6 Hz, 1H), 6.85 (d, J=8.0 Hz, 2H), 6.66 (d, J=8.0 Hz, 2H), 6.56 (m, 1H), 6.15 (d, J=7.6 Hz, 1H), 4.85 (dd, J=13.2, 5.6 Hz, 1H), 3.58 (s, 3H, 3.17 (d, J=5.2 Hz, 2H), 2.73 (m, 2H), 2.32 (m, 2H) ppm. $^{13}$CNMR(CDCl$_3$) δ 172.8, 172.4, 154.6, 136.0, 131.7, 129.3, 127.3, 123.0, 122.0, 119.5, 118.2, 115.4, 111.3, 109.2, 52.9, 52.4, 38.2, 30.4, 27.3 ppm.

EXAMPLE 6

Preparation of 2-[3-(4-hydroxyphenyl)propionylamino]pentanedioic acid diethyl ester Following the same procedure of Example 4 except that 3-(4-hydroxyphenyl)propionic acid (1.0 g, 6.0 mmol) and glutamic acid diethyl ester (1.34 g, 6.6 mmol) were used, 1.9 g of the title compound was obtained. The compound was finally purified by silica gel column chromatography (column size: 25 mm×150 mm, silica gel 70-230 mesh, eluent: hexane/EtOAc (1/1)). The results of analyses of the compound are as follows:

$^1$H NMR (CDCl$_3$) δ 7.02 (d, J=8.4 Hz, 2H), 6.74 (d, J=8.4 Hz, 2H), 6.23 (d, J=7.6 Hz, 1H), 4.58 (td, J=7.6, 5.2 Hz, 1H), 4.22–4.09 (m, 4H), 2.87 (m, 2H), 2.46 (m, 2H), 2.27 (m, 2H), 2.14 (m, 1H), 1.91 (m, 1H), 1.25 (m, 6H) ppm. $^{13}$C NMR (CDCl$_3$) δ 173.0, 172.4, 171.9, 154.5, 132.0, 129.3, 115.4, 61.7, 60.8, 51.6, 38.4, 30.6, 30.1, 27.2, 14.1, 14.0 ppm.

EXAMPLE 7

Preparation of 2-[3-(4-hydroxyphenyl)propionylamino]-4-methylsulfanyl butyric acid methyl ester Following the same procedure of Example 4 except that 3-(4-hydroxyphenyl)propionic acid (1.0 g, 6.0 mmol) and methionine methyl ester (1.08 g, 6.6 mmol) were used, 1.7 g of the title compound was obtained. The compound was finally purified by silica gel column chromatography (column size: 25 mm×150 mm, silica gel 70-230 mesh, eluent: hexane/EtOAc (1/1)). The results of analyses of the compound are as follows:

$^1$H NMR (CDCl$_3$) δ 7.02 (d, J=8.4 Hz, 2H), 6.75 (d, J=8.4 Hz, 2H), 6.67 (s,1H), 6.25 (d, J=8.0 Hz, 1H), 4.69 (dd, J=12.4, 7.2 Hz, 1H), 3.73 (s, 3H), 2.88 (m, 2H), 2.50 (m, 2J), 2.35 (m, 2H), 2.09 (m, 1H), 2.04 (s, 3H), 1.90 (m, 1H) ppm. $^{13}$C NMR (CDCl$_3$) δ 172.5, 172.4, 154.6, 131.8, 129.3, 115.4, 52.5, 51.4, 38.4, 31.4, 30.6, 29.7, 15.3 ppm.

EXAMPLE 8

Preparation of 2-[3-(4-hydroxyphenyl)propionylamino]acetic acid ethyl ester

Following the same procedure of Example 4 except that 3-(4-hydroxyphenyl)propionic acid (1.0 g, 6.0 mmol) and glycine ethyl ester hydrochloride (0.94 g, 6.7 mmol) were used, 1.4 g of the title compound was obtained. The compound was finally purified by silica gel column chromatography (column size: 25 mm×150 mm, silica gel 70-230 mesh, eluent: hexane/EtOAc (1/1)). The results of analyses of the compound are as follows:

$^1$H NMR (CDCl$_3$) δ 6.99 (d, J=8.8 Hz, 2H), 6.74 (d, J=8.8 Hz, 2H), 6.71 (s, 1H), 6.14 (br s, 1H), 4.19 (q, J=6.8 Hz, 2H), 3.99 (d, J=5.2 Hz, 2H), 2.87 (t, J=8.0 Hz, 2H), 2.50 (t, J=8.0 Hz, 2H), 1.26 (t, J=6.8 Hz, 3H) ppm. $^{13}$CNMR (CDCl$_3$) δ 172.9, 170.0, 154.6, 131.9, 129.2, 115.4, 61.6, 41.4, 38.2, 30.5, 14.0 ppm.

EXAMPLE 9

Preparation of 2-[3-(4-hydroxyphenyl)propionylamino]-3-methyl butyric acid methyl ester Following the same procedure of Example 4 except that 3-(4-hydroxyphenyl)propionic acid (1.0 g, 6.0 mmol) and valine methyl ester hydrochloride (1.1 g, 6.6 mmol) were used, 1.5 g of the title compound was obtained. The compound was finally purified by silica gel column chromatography (column size: 25 mm×150 mm, silica gel 70-230 mesh, eluent: hexane/EtOAc (1/1)). The results of analyses of the compound are as follows:

$^1$H NMR (CDCl$_3$) δ 7.02 (d, J=8.0 Hz, 2H), 6.75 (d, J=8.0 Hz, 2H), 6.61 (br s, 1H), 6.01 (br d, J=8.4 Hz, 1H), 4.53 (dd, J=8.8, 5.2 Hz, 1H), 3.71 (s, 3H), 2.88 (t, J=7.6 Hz, 2H), 2.52 (td, J=7.6, 3.6 Hz, 2H), 2.07 (m, 1H), 0.84 (d, J=6.8 Hz, 3H), 0.82 (d, J=6.8 Hz, 3H) ppm. $^{13}$C NMR (CDCl$_3$) δ 172.6, 154.6, 131.8, 129.3, 115.4, 57.0, 52.1, 38.4, 31.1, 30.7, 18.7, 17.7 ppm.

EXAMPLE 10

Preparation of
2-[3-(4-hydroxyphenyl)propionylamino]-3-phenyl
propionic acid

2-[3-(4-hydroxyphenyl)propionylamino]-3-phenyl propionic acid methyl ester (200 mg), prepared in Example 4, was dissolved in tetrahydrofuran (10 mL) and treated with 2M lithium hydroxide (1 mL). The resulting mixture was stirred for 18 hours at room temperature. The reaction was neutralized with aqueous hydrochloric acid, extracted with ethylacetate (EtOAc) (100 mL), dried over magnesium sulfate, concentrated under reduced pressure and purified by silica gel column chromatography (column size: 25 mm×150 mm, silica gel 70-230 mesh, eluent: EtOAc) to obtain 150 mg of the title compound. The yield was 78%. The results of analyses of the compound are as follows:

$^1$H NMR (DMSO-d6) δ 12.63 (br s, 1H), 9.12 (br s, 1H), 8.15 (d, J=8.0 Hz, 1H), 7.25 (m, 2H), 7.20 (m, 3H), 6.92 (d, J=8.0 Hz, 2H), 6.63 (d, J=8.0 Hz, 2H), 4.43 (m, 1H), 3.04 (dd, J=13.6, 4.4 Hz, 1H), 2.84 (dd, J=13.6, 9.2 Hz, 1H), 2.61 (t, J=8.0 Hz, 2H), 2.30 (t, J=8.0 Hz, 2H) ppm. $^{13}$C NMR (DMSO-d6) δ 173.6, 172.1, 155.9, 138.2, 131.8, 129.6, 129.5, 128.6, 126.8, 115.5, 53.8, 37.6, 37.3, 30.6 ppm.

EXAMPLE 11

Preparation of
2-[3-(4-hydroxyphenyl)propionylamino]-3-methyl
butyric acid

2-[3-(4-hydroxyphenyl)propionylamino]-3-methyl butyric acid methyl ester (200 mg), prepared in Example 9, was dissolved in tetrahydrofuran (10 mL) and treated with 2M lithium hydroxide (1 mL). The resulting mixture was stirred for 18 hours at room temperature. The reaction was neutralized with aqueous hydrochloric acid, extracted with ethylacetate (EtOAc) (100 mL), dried over magnesium sulfate, concentrated under reduced pressure and purified by silica gel column chromatography (column size: 25 mm×150 mm, silica gel 70-230 mesh, eluent: EtOAc) to obtain 160 mg of the title compound. The yield was 84%. The results of analyses of the compound are as follows:

$^1$H NMR (DMSO-d6) δ 12.49 (br s, 1H), 9.10 (s, 1H), 7.93 (d, J=8.8 Hz, 1H), 6.99 (d, J=8.8 Hz, 2H), 6.64 (d, J=8.8 Hz, 2H), 4.14 (dd, J=8.0, 6.0 Hz, 1H), 2.69 (t, J=8.0 Hz, 2H), 2.39 (m, 2H), 1.99 (m, 1H), 0.84 (d, J=4.0 Hz, 3H), 0.82 (d, J=4.0 Hz, 3H) ppm. $^{13}$C NMR (DMSO-d6) δ 173.6, 172.3, 155.8, 131.8, 129.5, 115.4, 57.5, 37.4, 30.8, 30.3, 19.5, 18.5 ppm.

Experimental Example 1

Effect of Phenolic Acid Derivatives Reducing
Blood Lipid Level

In order to confirm the effect of the phenolic acid derivatives of the present invention, an experiment consisting of the following steps was carried out using the compound prepared in Example 2 (BN30028).

Step 1: Administration of Lovastatin and BN30028 to Rats 30 of 4-week-old male white Sprague-Dawley rats (Bio Genomics Inc., Korea), each weighing about 90 to 10 g, were divided into three groups by a randomized block design. The rats of the three groups were fed with three different high-cholesterol diets, i.e., AIN-76 laboratory animal diets (TEKLAD premier Co., Madison, Wis., U.S.A.) containing 1% cholesterol (Control group), 1% cholesterol plus 0.02% lovastatin (Choongwae Pharma. Corp., Korea) and 1% cholesterol plus 0.046% BN30028, respectively, as shown in Table I.

TABLE I

| | Dietary group | | |
|---|---|---|---|
| Component | Control | Lovastatin group | BN30028 group |
| Casein | 20 | 20 | 20 |
| D,L-methionine | 0.3 | 0.3 | 0.3 |
| Corn starch | 15 | 15 | 15 |
| Cholesterol | 1 | 1 | 1 |
| Cellulose powder | 5 | 5 | 5 |
| Mineral mixture*1 | 3.5 | 3.5 | 3.5 |
| Vitamin mixture*2 | 1 | 1 | 1 |
| Choline bitartrate | 0.2 | 0.2 | 0.2 |
| Corn oil | 5 | 5 | 5 |
| Sucrose | 49 | 48.98 | 48.954 |
| Lovastatin | — | 0.02 | — |
| BN30028 | — | — | 0.046 |
| Total | 100 | 100 | 100 |

*1: AIN-76 mineral mixture (TEKLAD premier Co., Madison, WI, U.S.A.)
*2: AIN-76 vitamine mixture (TEKLAD premier Co., Madison, WI, U.S.A.)

The rats were allowed free access to the specified diets and water for 5 weeks and the ingestion amounts were recorded daily. The rats were weighed every 5 days, and then the record was analyzed. All rats showed a normal growth rate and there was observed no significant difference among the three groups in terms of the feed ingestion amount and the weight gain.

Step 2: Determination of Total Cholesterol, HDL-Cholesterol and Neutral Lipid Content in Blood The effects of administering lovastatin or BN30028 to rats on the plasma cholesterol and neutral lipid contents were examined as follows.

Blood samples were taken from vena hypogastrica of the rats of the three dietary groups raised in Step 1 and centrifuged to separate plasma. The total cholesterol level was measured by using a diagnosis kit purchased from Sigma (USA), Cat. No.: C0534, applying the method of Allain et al. (Allain et al., Clin. Chem., 20, 470-475 (1974)). The HDL fraction was separated by using a kit purchased from Sigma, Cat. No.: 352-1 applying the heparin-manganese precipitation method (Waenic R. G. and Albers J. J., J Lipid Res., 19, 65-76 (1978)) and the HDL-cholesterol level was measured by using a kit purchased from Sigma, Cat. No.: C9908. The triglyceride level was measured using a kit purchased from Sigma, Cat. No.: 336-10) applying the lipase-glycerol phosphate oxidase method (McGowan, M. W. et al., Clin. Chem., 29, 538-542(1983)). The total plasma cholesterol, HDL-cholesterol and triglyceride levels of three dietary groups are shown in Table II. All the data are expressed by average±standard deviation.

TABLE II

| | Dietary group | | |
|---|---|---|---|
| | Control | Lovastatin group | BN30028 group |
| Total cholesterol (mg/dL) | 82.1 ± 1.8 | 77.4 ± 1.8 | 72.8 ± 3.7 |
| HDL-cholesterol (mg/dL) | 22.44 ± 0.7 | 23.4 ± 0.4 | 25.6 ± 0.6 |

TABLE II-continued

| | Dietary group | | |
|---|---|---|---|
| | Control | Lovastatin group | BN30028 group |
| HDL-cholesterol/ total cholesterol (%) | 27.33 ± 0.8 | 30.2 ± 0.5 | 35.1 ± 0.6 |
| Triglyceride (mg/dL) | 55.5 ± 2.1 | 69.0 ± 4.7 | 47.6 ± 1.6 |
| Atherogenic index *(AI) | 2.65 ± 0.2 | 2.3 ± 0.2 | 1.84 ± 0.2 |

*Atherogenic index (AI) = (total cholesterol − HDL cholesterol)/HDL cholesterol

As can be seen from Table II, the administration of BN30028 reduced the total plasma cholesterol level and triglyceride by 12% and 15%, respectively, as compared to the control group, while the administration of lovastatin reduced the total plasma cholesterol level by 6% and increased triglyceride by 25%, as compared to the control group. Therefore, the BN30028 according to the present invention was demonstrated to be more effective to reduce the neutral fat level in blood than lovastatin which are currently used for the treatment of hyperlipidemia and thus is expected to be very useful in the prevention and treatment of hyperlipidemia casued by neutral fat.

Experimental Example 2

Inhibitory Effect of BN30028 on Arteriosclerosis in Rabbit

Step 1: Administration of BN30028 to Rabbits

Healthy male New Zealand White rabbits (Yeonam Horticulture and Animal Husbandry College, Korea), each weighing about 2.0 to 2.3 kg, were raised under a condition of temperature 20±2° C., relative humidity 55±10%, and photoperiod 12L/12D. The rabbits were divided into 3 groups, which were fed with 3 different diets, i.e., the control group fed with RC4 diet (Oriental Yeast Co., Japan) comprising moisture (7.6%), crude protein (22.8%), crude fat (2.8%), crude ash (8.8%), crude cellulose (14.4%) and soluble nitrogen-free substances (43.7%) plus cholesterol (1%) and two treatment groups further fed with lovastatin and BN30028 in addition to the feed of the control group. The rabbits were fed for 8 weeks while being allowed free access to the diets and water. The feed compositions and experiment regimens of the test groups are shown in Table III.

TABLE III

| Test group | Number of rabbit | Duration of administration | Dietary |
|---|---|---|---|
| Control group | 6 | 8 weeks | 1% cholesterol + RC4 diet |
| Lovastatin group | 6 | 8 weeks | 1% cholesterol + lovastatin (1 mg/kg) + RC4 diet |
| BN30028 group | 10 | 8 weeks | 1% cholesterol + BN30028 (0.05 wt %) + RC4 diet |

Step 2: Analysis for Fatty Streak in the Main Artery

The rabbits raised in Step 1 were sacrificed and their chests were incised. The incision was performed downward to the diaphragm along the aortic arch and the fat surrounding the main artery was removed. The main artery was incised in the middle along the longitudinal axis from the second aortic intercostal artery anastomoses to the seventh aortic intercostal artery anastomoses and fixed with 10% neutral buffered formalin for 24 hours. Then, the incised main artery was pinned to a dish for staining of fatty streaks according to the method of Esper, E., et al. (J. Lab. Clin. Med., 121, 103-110 (1993)). The staining carried out by washing the artery three times with propylene glycol for 2 minutes respectively. The artery was stained for 30 minutes with a saturated solution of Oil Red O (ORO, Sigma Co.) dissolved in propylene glycol. Thereafter, the artery was washed twice with 85% propylene glycol for 3 minutes respectively to remove the remaining staining solution and, then once with physiological saline. The artery was photographed and the photograph was traced. The proportion (%) of stained region (fatty streak region) per unit area of the main artery was determined with an image analyzer (LEICA, Q-600, Germany). The significant differences between the test groups were tested by student t-test using Microsoft excel (version 7.0) program As a result, it was shown that the proportions of the fatty streak region in the test groups treated with lovastatin and BN30028 were significantly reduced, as compared to the control group and BN30028 inhibited the fatty streak more effectively than lovastatin (Table IV).

TABLE IV

| Control group (n = 6) | Lovastatin group (n = 6) | BN30028 group (n = 10) |
|---|---|---|
| 50.0 ± 12.4[a] | 18.2 ± 10.4[b] | 16.1 ± 9.6[b] |

[a]data are expressed as 'average ± standard deviation'
[b]showing statistically significant difference from the control group (T-test, $p < 0.01$)

Figure 1B:
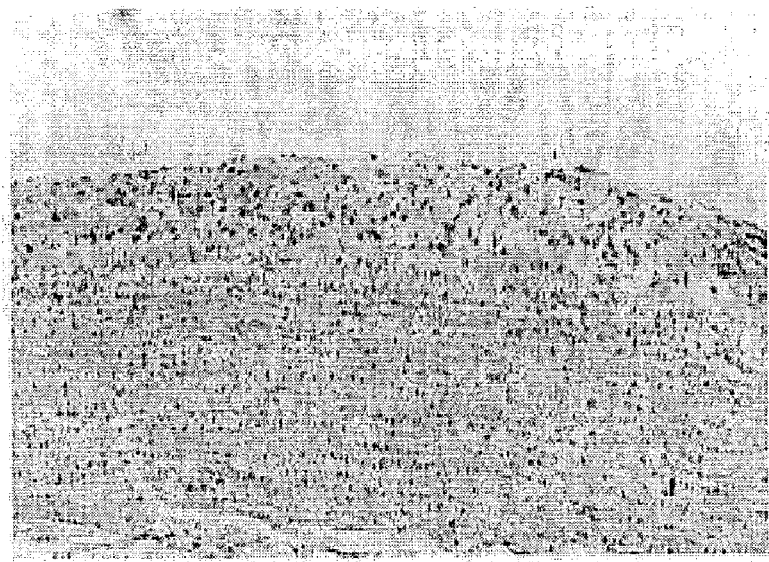
Figure 1C:
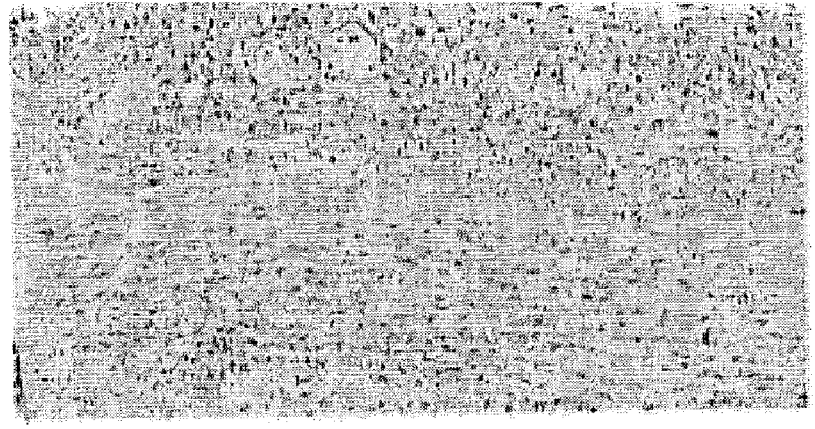

FIGS. 1a, 1b and 1c show photographs taken of the arterial endothelium of the control rabbit, and rabbits administered with lovastatin and BN30028, respectively. An atherosclerotic plaque formed of many macrophage-lipid complexes was observed on the arterial endothelium of the rabbit of the control group, as shown in FIG. 1a, while the arterial endothelia of the rabbits of the lovastatin group and BN30028 group are clean, which indicates that a macrophage-lipid complex was not formed. Therefore, it is noted that the phenolic acid derivatives of the present invention have strong effects of preventing arteriosclerosis even when the blood cholesterol level is high.

Step 3: Histologic Observation

In order to investigate effects of the compound of the present invention on the various organs and tissues of rabbit, the main artery, heart, lung, liver, kidney and muscle were taken from each of the rabbits upon autopsy and visually examined to confirm that no pathogenic abnormality was found. Thereafter, a piece of each organ was fixed in 10% neutral formalin for at least 24 hours. The fixed organ piece was washed sufficiently with tap water, dehydrated stepwise with 70%, 80%, 90% and 100% ethanol and, then, embedded in a paraffin by employing SHANDON, Histocentre 2, USA. The embedded organ piece was sectioned in a thickness of 4 μm with a microtome (LEICA, RM2045, Germany) and stained with H & E (hematoxylin and eosin). The stained organ specimen was made transparent with xylene, mounted with permount, and then observed under a microscope.

Experimental Example 3

Effect of BN30028 on Hepatic Diseases

In order to quantitatively evaluate the effects of feeding a high cholesterol diet with test substances on liver tissues, the liver specimens prepared in step 3 of the Experimental Example 3 were observed under a microscope with referring to the procedure described by Fogt F. et al. (Fogt F. and Nanji A., Toxicology and Applied Pharmacology, 136, 87-93, 1996) and the procedure described by Keegan et al. (Keegan A., et al., Journal of Hepatology 23: 591-600, 1995). The specimens were classified into for grades: 1+(0-25%), 2+(26-50%), 3+(51-75) and 4+(76-100%) according to the proportion of abnormal fat-containing cells in the liver lobules around the central vein. The significant differences between the test groups were tested by student t-test using Microsoft excel (version 7.0) program As a result, the proportion of fat-modified cells was significantly reduced in the BN30028 group (p<0.05). The results are shown in Table V.

TABLE V

| Control group (n = 6) | Lovastatin group (n = 6) | BN30028 group (n = 10) |
|---|---|---|
| 3.78 ± 0.13 | 3.97 ± 0.15 | 3.57 ± 0.35 |

Figure 2A:
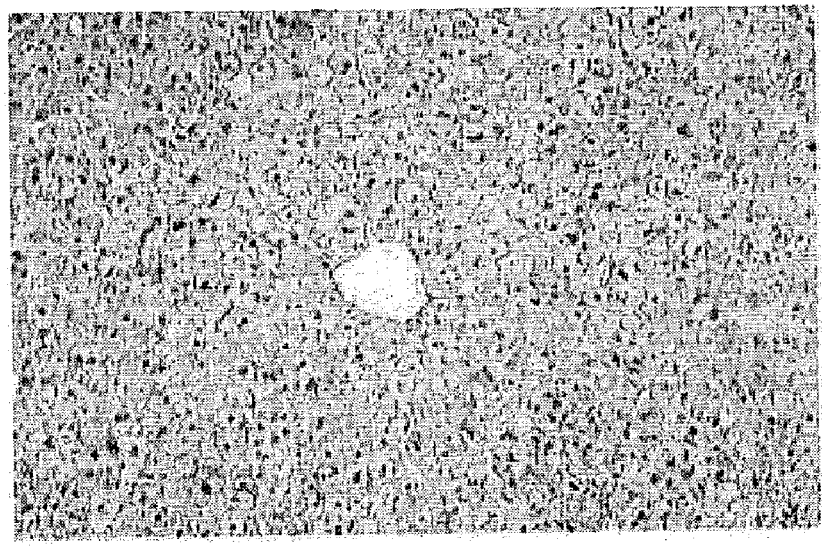
FIGS. 2a, 2b and 2c are microscopic photographs taken of the livers of the control rabbit, and rabbits administered with lovastatin and BN30028, respectively.
Figure 2B:
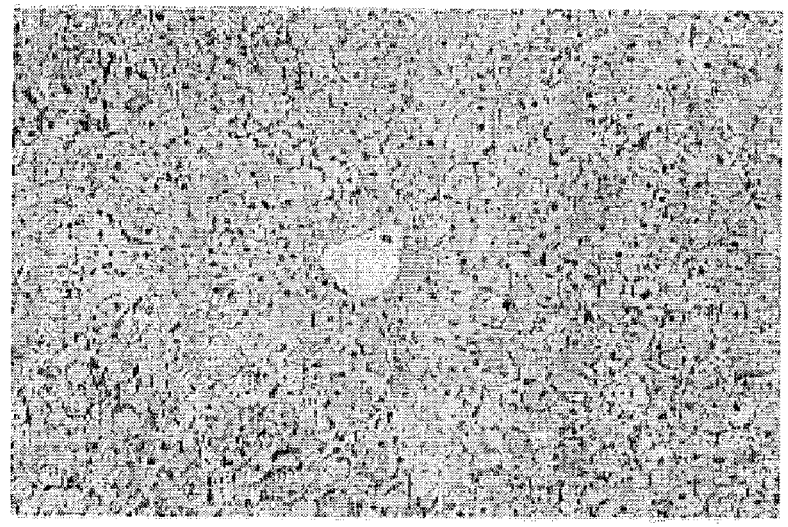
Figure 2C:
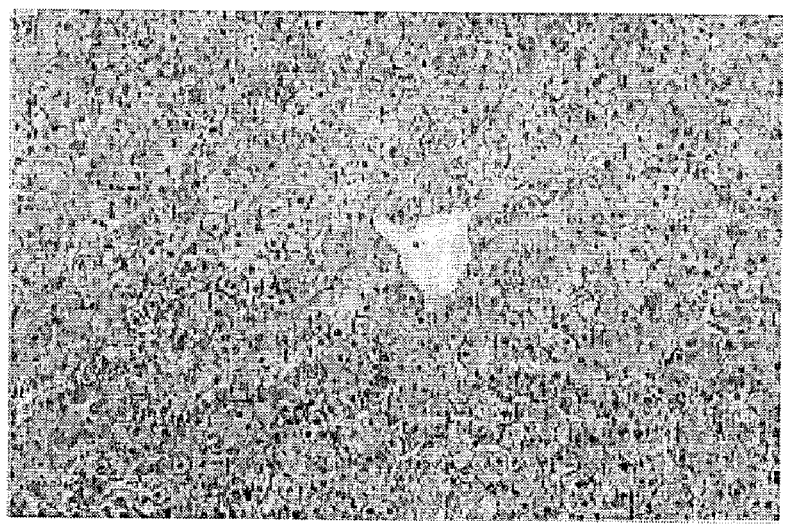
Figure 3A:
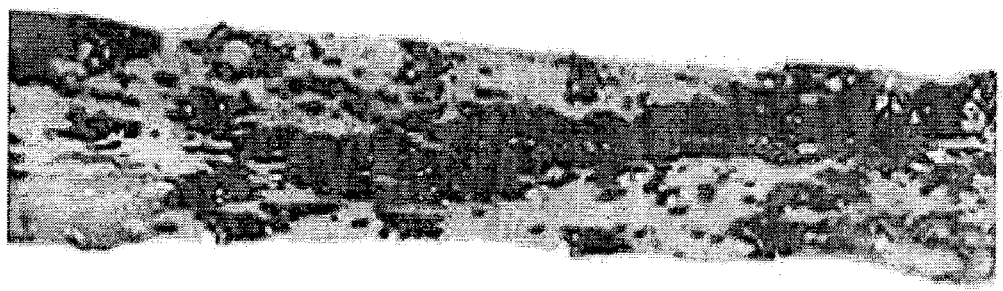
FIGS. 3a, 3b, 3c, 3d and 3e are photographs taken of the arterial fatty streak of the control rabbit, and rabbits administered with lovastatin, BN30063, BN30064 and BN30067, respectively (stained with oil red O)
Figure 3B:
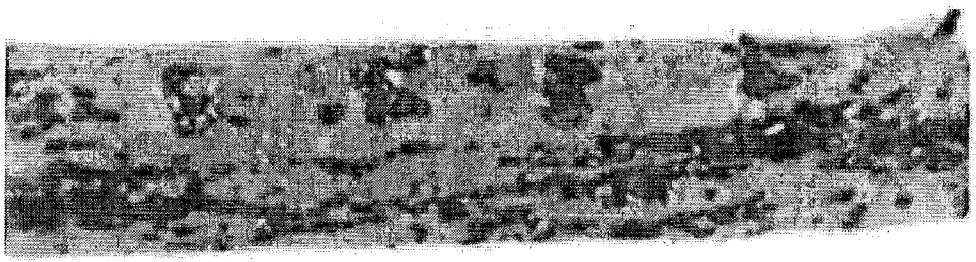
Figure 3C:
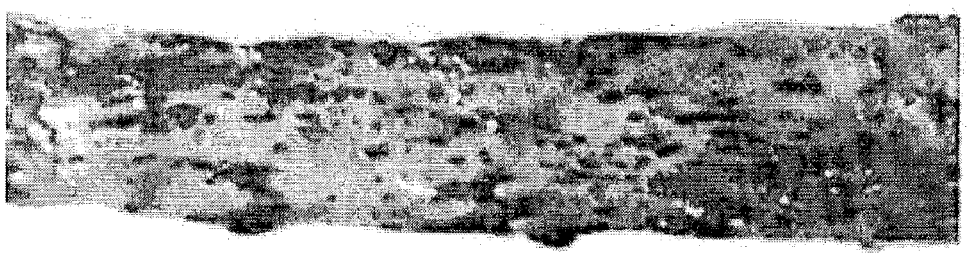
Figure 3D:
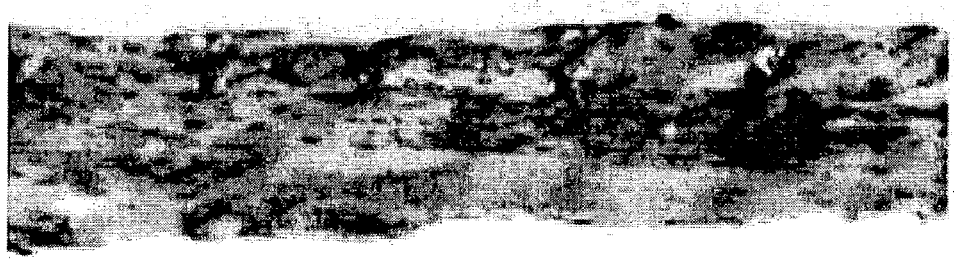
Figure 3E:
Figure 4A:
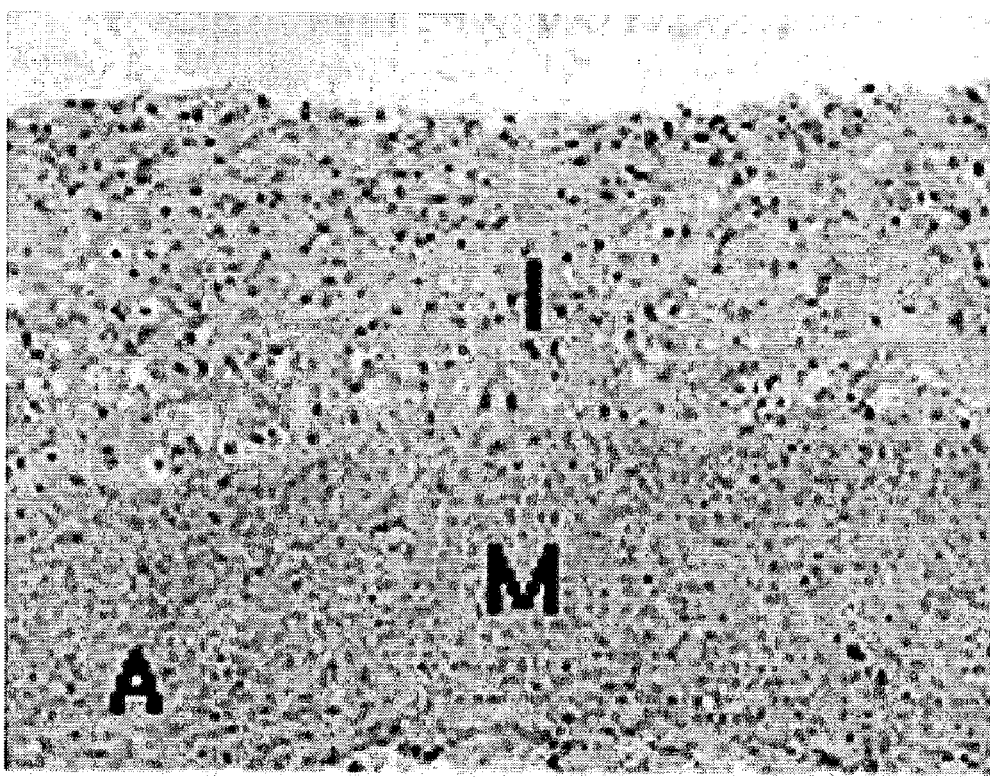
FIGS. 4a, 4b and 4c are photographs taken of the arterial endothelium of the control rabbit, and rabbits administered with lovastatin and BN30064, respectively (I=Intima, M=Media, stained with H & E×100)
Figure 4B:
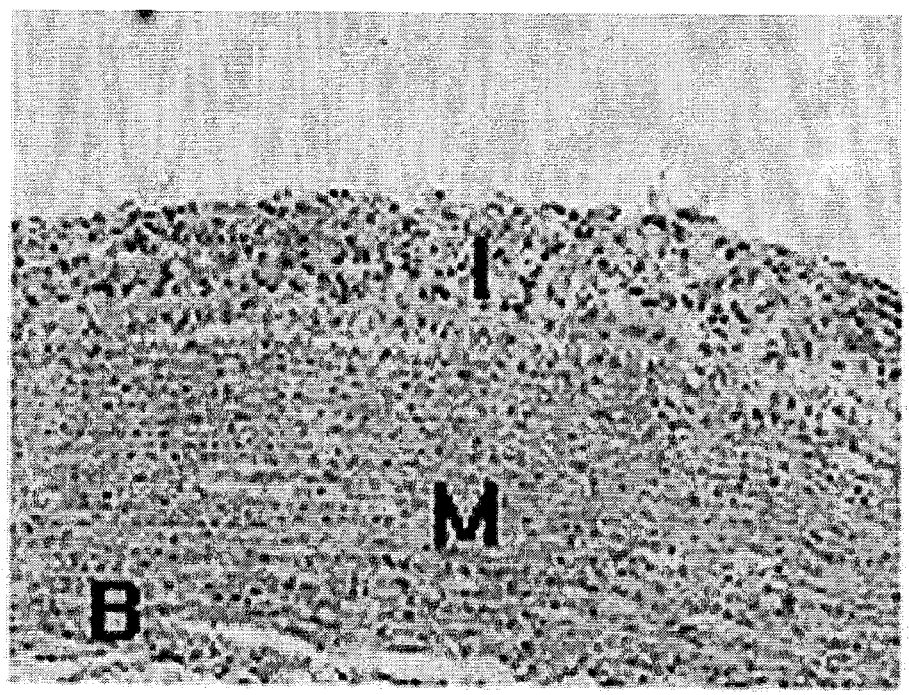
Figure 4C:
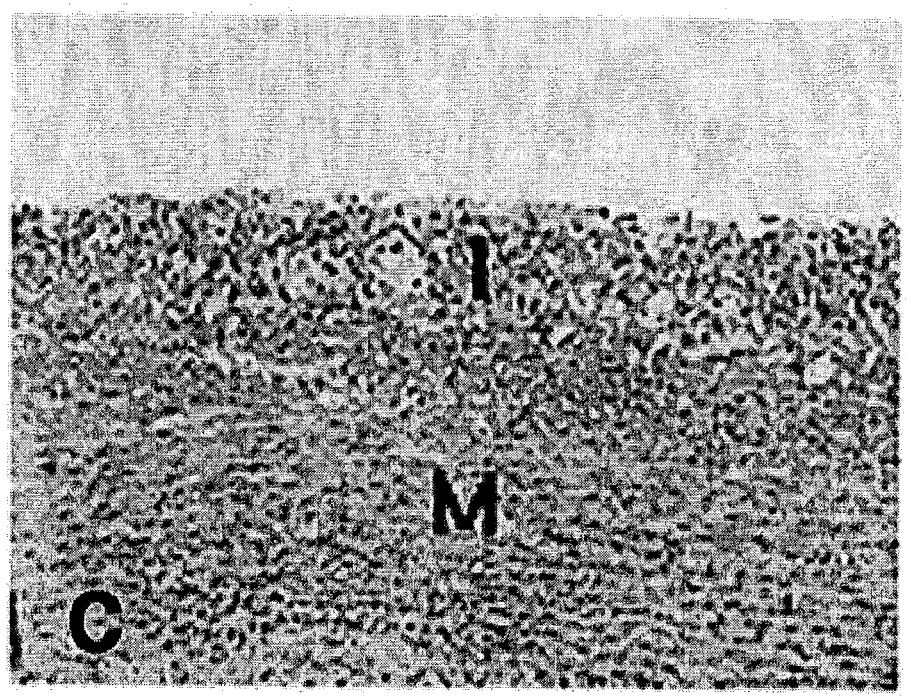
Figure 5A:
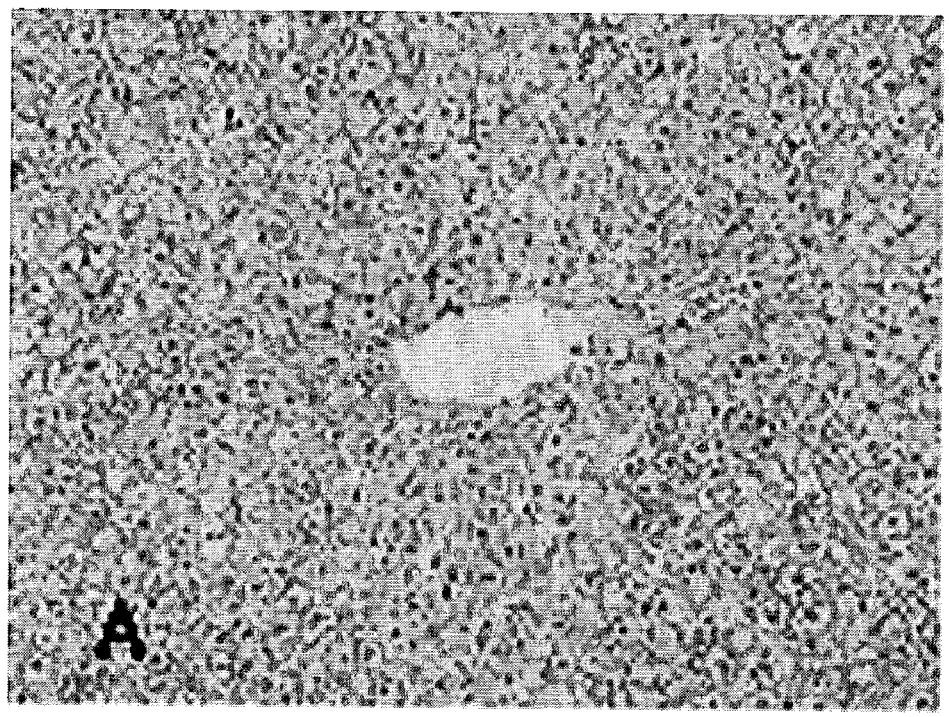
FIGS. 5a, 5b and 5c are microscopic photographs taken of dissected liver of the control rabbit, and rabbits administered with lovastatin and BN30064, respectively (stained with H & E×100).
Figure 5B:
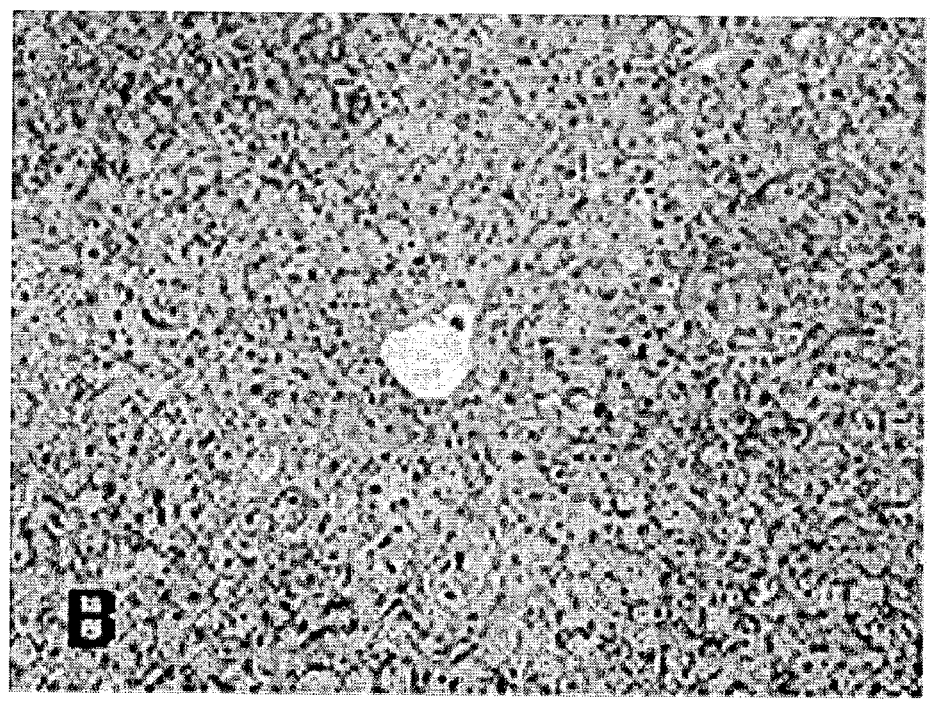
Figure 5C:
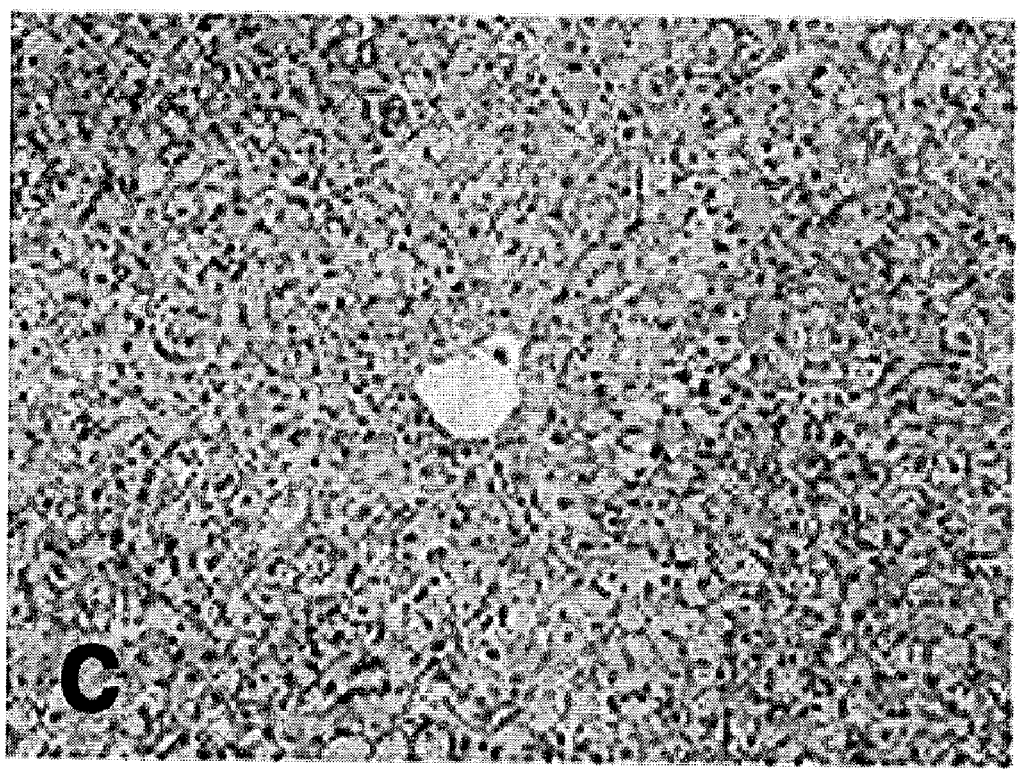

FIGS. 2a, 2b and 2c show the microscopic photographs taken of the livers of the control rabbit, and rabbits administered with lovastatin and BN30028. As shown in FIGS. 2a and 2b, many cells containing excessive fat were observed around the central vein in the livers of the control rabbits and the rabbits administered with lovastatin. In contrast, almost all liver cells of the rabbits administered with BN30028 are of a normal shape as shown in FIG. 2c. Therefore, it was noted that BN30028 of the present invention can strongly inhibit the formation of fatty liver.

Experimental Example 4

Effect of BN30028 on Inhibition of ACAT Activity in Rabbit

Step 1: Preparation of Microsomes

In order to confirm the effect of BN30028 on inhibition of ACAT enzymatic activity, microsomes were separated from liver tissues to be used as an enzyme source.

The rabbits raised as described in step 1 of the Experimental Example 2 were sacrificed by decapitation and the livers were removed from the rabbits. 1 g of the liver tissue taken from each rabbit was homogenized in 5 ml of homogenization medium (0.1 M $KH_2PO_4$, pH 7.4, 0.1 mM EDTA and 10 mM β-mercaptoethanol). The homogenate was centrifuged at 3,000×g for 10 minutes at 4° C. and the supernatant thus obtained was centrifuged at 15,000×g for 15 minutes at 4° C. to obtain a supernatant. The resulting supernatant was put into an ultracentrifuge tube (Beckman) and centrifuged at 100,000×g for 1 hour at 4° C. to obtain microsomal pellets, which were then suspended in 3 ml of the homogenization medium and centrifuged at 100,000×g for 1 hour at 4° C. The pellets thus obtained were suspended in 1 ml of the homogenization medium. The protein concentration of the resulting suspension was determined by Lowry's method and then adjusted to the range of 4 to 8 mg/ml. The resulting suspension was stored in a deep freezer (Biofreezer, Forma Scientific Inc.).

Step 2: Measurement of ACAT Activity 6.67 μl, of 1 mg/ml cholesterol solution in acetone was mixed with 6 μl of 10% Triton WR-1339 (Sigma Co.) in acetone. Acetone was removed from the mixture by evaporation under a nitrogen flow. To the resulting mixture, distilled water was added to adjust the concentration of cholesterol to 30 mg/ml.

To 10 μl of the resulting aqueous cholesterol solution, 10 μl of 1 M $KH_2PO_4$ (pH 7.4), 5 μl of 0.6 mM bovine serum albumin (BSA), 10 μl of the microsome solution obtained in Step 1 and 55 μl of distilled water (total 90 μl) were added. The mixture was pre-incubated in a water bath at 37° C. for 30 minutes.

10 μl of ($1-^{14}C$) oleyl-CoA solution (0.05 μCi, final concentration: 10 μM) was added to the pre-incubated mixture and the resulting mixture was incubated in a water bath at 37° C. for 30 minutes. 500 μl of isopropanol:heptane mixture (4:1 (v/v)), 300 μl of heptane and 200 μl of 0.1 M $KH_2PO_4$ (pH 7.4). were added to the mixture. The mixture was mixed vigorously using a vortex mixer and then allowed to stand at room temperature for 2 minutes.

200 μl of the resulting supernatant was put in a scintillation bottle and 4 ml of scintillation fluid (Lumac) was added thereto. The mixture was assayed for radioactivity with 1450 Microbeta liquid scintillation counter (Wallacoy, Finland). ACAT activity was calculated as picomoles of cholesteryl oleate synthesized per minute per mg protein (pmoles/min/mg protein). All the data are expressed by average±standard deviation(p<0.05). The results are shown in Table VI.

TABLE VI

| | Inhibition on ACAT activity (average ± standard deviation) | |
|---|---|---|
| Test groups | ACAT activity (pmol/minute/mg protein) | ACAT activity inhibition (%) |
| BN30028 group | 93.9 ± 21.5 | 26.2 |
| Lovastatin group | 96.2 ± 21.3 | 23.8 |
| Control group | 126.5 ± 10.0 | 0 |

As can be seen from Table VI, inhibition of ACAT activities observed in the BN30028 group was 26.2%, which is higher than that of the control group, 23.8%.

Experimental Example 5

Toxicity of BN30028 Orally Administered

The toxicity of orally administered BN30028 was tested as follows. Four-week-old specific pathogen-free ICR mice, 12 female mice and 12 male mice, were kept in a room under conditions of 22±3° C., 55±10% relative humidity and 12L/12D photoperiod. The mice was acclimated for one week before using in experiment. Fodder (Cheiljedang Co., mouse and rat fodder) and water were sterilized and freely fed to the mice.

BN30028 was dissolved in 0.5% Tween 80 to a concentration of 100 mg/ml and the solution was orally administered to the mice in an amount of 0.2 mL (1 g/kg), 0.4 mL (2 g/kg) or 0.8 mL (4 g/kg) per 20 g of mouse body weight. The solution was administered once for the 1 g/kg and 2 g/kg groups and twice for the 4 g/kg group. The animals were observed for 7 days for signs of adverse effects or death according to the following schedule: 1, 4, 8, and 12 hours after the administration on the day of the administration, and at least once in the morning and afternoon from the 2nd day to the 7th day after the administration, the changes of the conditions and death were observed. Also, on the 7th day, the mice were sacrificed and the internal organs were visually examined. From the day of the administration, the weight changes of the animals were recorded every other day to examine the effect of BN30028 on the reduction of body weight of animals.

As a result, in the acute oral toxicity test, all the mice of the groups treated with BN30028 in amounts of 1 g/kg, 2 g/kg and 4 g/kg were alive until the 7th day. After 7 days had passed, the autopsy revealed that the mice had not developed any pathological abnormality, and showed normal weight increase without any weight loss for 7 days after the administration.

Accordingly, it was concluded that $LD_{50}$ of BN30028 orally administered is more than 4 g/kg body weight for both female and male mice.

EXAMPLE 12

Preparation of 2-[3-(3,4-dihydroxyphenyl)propionylamino]-3-hydroxy propionic acid methyl ester (BN30063)

Following the same procedure of Example 1 except that 3,4-dihydroxyphenyl propionic acid (1.8 g, 9.6 mmol) and serine methyl ester (1.5 g, 9.6 mmol) were used, 1.0 g of the title compound was obtained. The compound was finally purified by silica gel column chromatography (column size: 25 mm×150 mm, silica gel 70-230 mesh, eluent: hexane/EtOAc (1/2)). The results of analyses of the compound are as follows:

$^1$H NMR (Acetone-d8) 7.70 (s, 1H), 7.64 (s, 1H), 7.29 (d, J=7.2Hz, 1H), 6.71 (d, J=2.4 Hz, 1H), 6.70 (d, J=8.0 Hz, 1H), 6.55 (dd, J=8.0, 2.4 Hz, 1H), 4.54 (m, 1H), 3.88 (m, 1H), 3.76 (m, 1H), 3.67 (s, 3H), 2.77 (d, J=9.6 Hz, 1H), 2.76 (d, J=8.4 Hz, 1H), 2.51 (d, J=8.0 Hz, 1H), 2.50 (d, J=9.6 Hz, 1H) ppm. $^{13}$C NMR (Acetone-d8) 172.1, 171.1, 145.0, 143.4, 133.3, 119.6, 115.6, 115.3, 62.4, 54.9, 51.5, 37.9, 31.0 ppm.

EXAMPLE 13

Preparation of 2-[3-(3,4-dihydroxyphenyl)propionylamino]-4-methyl pentanoic acid methyl ester Following the same procedure of Example 1 except that 3,4-dihydroxyphenyl propionic acid (1.5 g, 8.3 mmol) and leucine methyl ester (1.5 g, 8.3 mmol) were used, 1.6 g of the title compound was obtained. The compound was finally purified by silica gel column chromatography (column size: 25 mm×150 mm, silica gel 70-230 mesh, eluent: hexane/EtOAc (1.5/1)). The results of analyses of the compound are as follows:

$^1$H NMR (MeOH-d4) 6.65 (d, J=8.0 Hz, 1H), 6.62 (d, J=2.4 Hz, 1H), 6.51 (dd, J=8.0, 1.6 Hz, 1H), 4.40 (t, J=7.2 Hz, 1H), 3.67 (s, 3H), 2.75 (t, J=7.6 Hz, 2H), 2.46 (t, J=7.6 Hz, 2H), 1.48 (m, 3H), 0.88 (d, J=6.0 Hz, 3H), 0.84 (d, J=6.4 Hz, 3H) ppm. $^{13}$C NMR (MeOH-d4) 174.3, 173.59, 145.0, 143.4, 132.37, 119.4, 115.4, 115.1, 51.4,50.8, 40.2, 37.7, 31.1, 24.6, 22.1, 20.5 ppm.

EXAMPLE 14

Preparation of 2-[3-(3,4-dihydroxyphenyl)propionylamino]-succinic acid dibenzyl ester Following the same procedure of Example 1 except that 3,4-dihydroxyphenyl propionic acid (8 g, 43.9 mmol) and aspartic acid dibenzyl ester (15.1 g, 48.3 mmol) were used, 12 g of the title compound was obtained. The compound was finally purified by silica gel column chromatography (column size: 25 mm×150 mm, silica gel 70-230 mesh, eluent: hexane/EtOAc (2/1)). The results of analyses of the compound are as follows:

$^1$H NMR (CDCl$_3$) 7.31 (m, 10H), 6.74 (d, J=8.0 Hz, 1H), 6.66 (d, J=1.6 Hz, 1H), 6.55 (dd, J=8.0, 2.0 Hz, 1H), 6.49 (d, J=7.6 Hz, 1H), 5.10 (s, 2H), 5.05 (d, J=12Hz, 1H), 5.00 (d, J=12 Hz, 2H), 4.87 (m, 1H), 3.02 (dd, J=16.8, 4.4 Hz, 1H), 2.83-2.77 (m, 2H), 2.43 (m, 2H), ppm. $^{13}$C NMR (CDCl$_3$) 172.9, 171.1, 170.7, 143.9, 142.8, 135.4, 135.2, 133.0, 128.9, 128.8, 128.7, 128.6, 128.5, 120.7, 115.6, 115.5, 67.9, 67.2, 48.9 ppm.

EXAMPLE 15

Preparation of 2-[3-(3,4-dihydroxyphenyl)propionylamino]-4-methyl pentanoic acid (BN30064)

2-[3-(3,4-dihydroxyphenyl)propionylamino]-4-methyl pentanoic acid methyl ester (200 mg), prepared in Example 13, was dissolved in tetrahydrofuran (5 mL) and treated with 2M lithium hydroxide (1 mL). The resulting mixture was stirred for 18 hours at room temperature. The resulting reaction was neutralized with aqueous hydrochloric acid, extracted with ethylacetate (EtOAc) (100 mL), dried over magnesium sulfate, concentrated under reduced pressure and purified by silica gel column chromatography (column size: 25 mm×150 mm, silica gel 70-230 mesh, eluent: hexan/EtOAc (1/5)) to obtain 184.5 mg of the title compound. The yield was 97%. The results of analyses of the compound are as follows:

$^1$H NMR (MeOH-d4) 6.65 (d, J=8.4 Hz, 1H), 6.62 (d, J=2.0 Hz, 1H), 6.51 (dd, J=8.2, 2.4 Hz, 1H), 4.38 (t, J=7.6 Hz, 2H), 2.75 (t, J=8.0 Hz, 2H), 2.46 (t, J=7.4, Hz, 2H), 1.55–1.20 (m, 3H), 0.87 (dd, J=17.6, 6.8 Hz, 6H) ppm. $^{13}$C NMR (MeOH-d4) 175.0, 174.3, 145.0, 143.4, 132.4, 119.4, 115.4, 115.1, 50.7, 40.4, 37.9, 31.1, 24.6, 22.3, 19.7 ppm.

EXAMPLE 16

Preparation of 2-[3-(3,4-dihydroxyphenyl)propionylamino]-succinic acid (BN30067)

2-[3-(3,4-dihydroxyphenyl)propionylamino]-succinic acid dibenzyl ester (12 g), prepared in Example 14, was dissolved in tetrahydrofuran (100 mL) and treated with 2M lithium hydroxide (126 mL). The resulting mixture was stirred for 18 hours at room temperature. The resulting reaction was neutralized with aqueous hydrochloric acid, extracted with ethylacetate (EtOAc) (500 mL), dried over magnesium sulfate, concentrated under reduced pressure and purified by silica gel column chromatography (column size: 25 mm×150 mm, silica gel 70-230 mesh, eluent:

MC/MeOH (5/95)) to obtain 4.28 g of the title compound. The yield was 57%. The results of analyses of the compound are as follows:

$^1$H NMR (MeOH-d4) 6.65 (d, J=8.0 Hz, 1H), 6.63 (d, J=2.4 Hz, 1H), 6.52 (dd, J=7.8, 2 Hz, 1H), 4.72 (t, 5.8 Hz, 1H), 2.82–2.69 (m, 4H), 2.48–2.43 (m, 2H) ppm. $^{13}$C NMR (MeOH-d4) 174.1, 173.1, 172.9, 145.0, 143.4, 132.6, 119.4, 115.3, 115.2, 49.0, 38.0, 35.8, 31.1 ppm.

EXAMPLE 17

Preparation of 2-[3-(3,4-dihydroxyphenyl)propionyl]pyrrolidine-2-carboxylic acid ethyl ester Following the same procedure of Example I except that 3,4-dihydroxyphenyl propionic acid (1.0 g, 5.5 mmol) and proline ethyl ester (0.86 g ,6.1 mmol) were used, 1.7 g of the title compound was obtained. The compound was finally purified by silica gel column chromatography (column size: 25 mm×150 mm, silica gel 70-230 mesh, eluent: hexane/EtOAc (1/2)). The results of analyses of the compound are as follows:

$^1$H NMR (CDCl$_3$) 7.15 (s, 1H), 6.77 (d, J=8.0 Hz, 1H), 6.74 (d, J=2.0 Hz, 1H), 1H), 6.58 (dd, J=8.0, 2.0 Hz, 1H), 5.97 (s, 1H), 4.48 (dd, J=8.8, 4.0 Hz, 1H), 4.18 (q, J=6.8 Hz, 2H), 3.44 (m, 1H), 3.33 (m, 1H), 2.83 (m, 2H), 2.56 (m, 2H), 2.13 (m, 1H), 1.95 (m, 3H), 1.25 (t, J=6.8 Hz, 3H) ppm.

Experimental Example 6

Effect of Phenolic Acid Derivatives (BN30063, BN30064, BN30067) on Hyperlipemia in Rat Step 1: Administration of Lovastatin and Phenolic Acid Derivatives BN30063, BN30064, BN30067 to Rats 50 of 4-week-old male white Sprague-Dawley rats (Bio Genomics Inc., Korea), each weighing about 90 to 110 g, were divided into five groups by a randomized block design. The rats of the five groups were fed with five different high-cholesterol diets, i.e., AIN-76 laboratory animal diets (TEKLAD premier Co., Madison, Wis., U.S.A.) containing 1% cholesterol (Control group), 1% cholesterol plus 0.02% lovastatin (Choongwae Pharma. Corp., Korea), 1% cholesterol plus 0.039% BN30063, 1% cholesterol plus 0.040% BN30064, and 1% cholesterol plus 0.041% BN30067, respectively, as shown in Table VII.

TABLE VII

| Component | Dietary group | | | | |
| --- | --- | --- | --- | --- | --- |
| | Control | Lovastatin group | BN30063 group | BN30064 group | BN30067 group |
| Casein | 20 | 20 | 20 | 20 | 20 |
| D,L-methionine | 0.3 | 0.3 | 0.3 | 0.3 | 0.3 |
| Corn starch | 15 | 15 | 15 | 15 | 15 |
| Sucrose | 49 | 48.980 | 48.961 | 48.960 | 48.959 |
| Cellulose powder | 5 | 5 | 5 | 5 | 5 |
| Mineral mixture*1 | 3.5 | 3.5 | 3.5 | 3.5 | 3.5 |
| Vitamin mixture*2 | 1 | 1 | 1 | 1 | 1 |
| Choline bitartrate | 0.2 | 0.2 | 0.2 | 0.2 | 0.2 |
| Corn oil | 5 | 5 | 5 | 5 | 5 |
| Cholesterol | 1 | 1 | 1 | 1 | 1 |
| Lovastatin | — | 0.02 | — | — | — |
| BN30063 | — | — | 0.039 | — | — |
| NN30064 | — | — | — | 0.040 | — |
| BN30067 | — | — | — | — | 0.041 |
| Total | 100 | 100 | 100 | 100 | 100 |

*1: AIN-76 mineral mixture (TEKLAD premier Co., Madison, WI, U.S.A.)
*2: AIN-76 vitamine mixture (TEKLAD premier Co., Madison, WI, U.S.A.)

The animals were allowed free access to the specified diets and water for 6 weeks and the ingestion amounts were recorded daily. The rats were weighed every 7 days, and then the record was analyzed. All rats showed a normal growth rate and there was observed no significant difference among the five groups in terms of the feed ingestion amount and the weight gain.

Step 2: Determination of Total Cholesterol, HDL-Cholesterol and Neutral Lipid Content in Blood The effects of administering lovastatin or the phenolic acid derivatives BN30063, BN30064, BN30067 to rats on the plasma cholesterol and neutral lipid contents were examined as follows.

Blood samples were taken from vena hypogastrica of the rats of the five dietary groups raised for six weeks in Step 1. The blood was allowed to stand for 2 hours and centrifuged at 3,000 rpm for 15 minutes and the supernatant containing serum was separated and stored in a deep freezer before use. The total cholesterol level was measured using a diagnosis kit purchased from Sigma, Cat. No.: C0534, applying the method of Allain et al. (Allain et al., *Clin. Chem.*, 20, 470-475 (1974)). The HDL fraction was separated using a kit purchased from Sigma, Cat. No.: 352-1 applying the heparin-manganese precipitation method (Waenic R. G. and Albers J. J., *J Lipid Res.*, 19, 65-76 (1978)) and the HDL-cholesterol level was measured using a kit purchased from Sigma, Cat. No.: C9908. The neutral fat level was measured using a kit purchased from Sigma, Cat. No.: 336-10) applying the lipase-glycerol phosphate oxidase method (McGowan, M. W. et al., *Clin. Chem.*, 29, 538-542(1983)).

The plasma cholesterol, HDL-cholesterol and neutral fat levels of five dietary groups are shown in Table VIII. All the data are expressed by average±standard deviation.

TABLE VIII

| | Dietary group | | | | |
| --- | --- | --- | --- | --- | --- |
| | Control | Lovastatin group | BN30063 group | BN30064 group | BN30067 group |
| Total cholesterol (mg/dL) | 96.97 ± 7.08 | 86.51 ± 8.28 | 68.06 ± 4.92 | 75.71 ± 3.69 | 69.99 ± 5.37 |
| HDL-cholesterol (mg/dL) | 25.71 ± 1.54 | 24.83 ± 1.92 | 28.97 ± 21.9 | 28.49 ± 2.13 | 23.81 ± 1.52 |
| HDL-cholesterol/total cholesterol (%) | 24.26 ± 1.94 | 29.13 ± 2.22 | 43.25 ± 2.73 | 40.78 ± 4.06 | 34.62 ± 2.06 |
| Neutral fat (mg/dL) | 103.42 ± 9.80 | 83.85 ± 11.38 | 52.31 ± 4.83 | 73.07 ± 4.34 | 37.37 ± 4.59 |

TABLE VIII-continued

| | Dietary group | | | | |
|---|---|---|---|---|---|
| | Control | Lovastatin group | BN30063 group | BN30064 group | BN30067 group |
| Atherogenic index *(AI) | 3.29 ± 0.36 | 2.58 ± 0.32 | 1.39 ± 0.15 | 1.61 ± 0.28 | 1.96 ± 0.18 |

*Atherogenic index (AI) = (total cholesterol − HDL cholesterol)/HDL cholesterol

As can be seen from Table VIII, the administration of phenolic acid derivatives (BN30063, BN30064, BN30067) reduced the total plasma cholesterol level by 29.8%, 21.92% and 27.82%, respectively, as compared to the control group. The rates of HDL-cholesterol to total cholesterol of the rats treated with phenolic acid derivatives (BN30063, BN30064, BN30067) were increased by 78.28%, 68.10% and 42.70%, respectively, as compared to the control group. The neutral fat levels of the rats treated with phenolic acid derivatives (BN30063, BN30064, BN30067) were reduced by 49.41%, 29.35% and 63.87%, respectively, as compared to the control group. Also, the atherogenic index of the rats treated with phenolic acid derivatives (BN30063, BN30064, BN30067) were reduced by 57.75%, 51.06% and 40.43%, respectively, as compared to the control group. In contrast, for the lovastatin-treated group, the total plasma cholesterol level was reduced by 10%, the HDL-cholesterol/total cholesterol was increased by 20%, the neutral fat was reduced by 18.92%, and the atherogenic index was reduced by 21.58%. From these results, the phenolic acid derivatives (BN30063, BN30064, BN30067) according to the present invention were demonstrated to be more effective to reduce the total plasma cholesterol and the neutral fat level in blood than lovastatin which are currently used for the treatment of hyperlipidemia and thus are expected to be very useful in the prevention and treatment of hyperlipidemia casued by neutral fat.

Step 3: Assay of ACAT Activity Inhibition 1 g of the liver tissue taken from each sacrificed rat of Step 1 was homogenized in 5 ml of the first homogenization medium {0.1 M $KH_2PO_4$(pH 7.4), 0.1 mM EDTA and 10 mM β-mercaptoethanol}. The homogenate was centrifuged at 3,000×g for 15 minutes at 4° C. and the supernatant thus obtained was put into a tube and centrifuged at 15,000×g for 15 minutes at 4° C. to obtain a supernatant. The resulting supernatant was put into a 5 mL ultracentrifuge tube (Beckman) and centrifuged at 100,000×g for 1 hour at 4° C. The supernatant was removed off and pellets thus obtained were suspended in 3 mL of the first homogenization medium and centrifuged at 100,000×g for 1 hour at 4° C. The resulting supernatant was removed off and pellets thus obtained were suspended in 1 ml of the first homogenization medium. The resulting suspension was stored in a deep freezer.

6.67 μl of 1 mg/ml cholesterol solution in acetone was mixed with 6 μl of 10% Triton WR-1339 (Sigma Co.) in acetone. Acetone was removed from the mixture by evaporation under a nitrogen flow. To the resulting mixture, distilled water was added to adjust the concentration of cholesterol to 300 mg/10 ml. 10 μl of the resulting aqueous cholesterol solution was mixed with 10 μl of 1 M $KH_2PO_4$ (pH 7.4), 5 μl of 0.6 mM bovine serum albumin (BSA), 10 μl of the microsome solution obtained as above and 55 μl of distilled water (total 90 μl). The mixture was pre-incubated in a water bath at 37° C. for 30 minutes.

10 μl of oleyl-CoA solution (0.3 m/mL) prepared by mixing radiolabelled oleyl-CoA with oleyl-CoA was added to the pre-incubated mixture and the resulting mixture was incubated in a water bath at 37° C. for 30 minutes. 500 μl of isopropanol:heptane mixture (4:1 (v/v)), 300 μl of heptane and 200 μl of 0.1 M $KH_2PO_4$ (pH 7.4) were added to the mixture. The mixture was mixed vigorously using a vortex mixer and then allowed to stand at room temperature for 2 minutes.

200 μl of the resulting supernatant was put in a scintillation bottle and 4 mL of scintillation fluid (Lumac) was added thereto. The mixture was assayed for radioactivity with a scintillation counter. ACAT activity was calculated from the measured radioactivity, which was used to determine the ACAT activity inhibition (%). The results are shown in Table IX.

TABLE IX

| Dietary group | Control group | Lovastatin group | BN30063 group | BN30064 group | BN30067 group |
|---|---|---|---|---|---|
| ACAT activity (pmol/ minute/mg protein) | 186.12 ± 9.48 | 166.66 ± 6.80 | 186.56 ± 10.00 | 152.49 ± 5.49 | 160.01 ± 5.77 |
| ACAT activity inhibition (%) | 0 | 10.46 | 0 | 18.07 | 14.03 |

As can be seen from Table IX, the ACAT activity inhibitions observed in the BN30064 and BN30067 groups were 14 to 18% lower than that of the control group.

Step 4: Measurement of HMG-CoA Reductase Activity

In order to measure the activity of HMG-CoA reductase, the method described by Hulcher et al. (J. Lipid Res., 14, 625-641 (1973)) was employed after some modification. In this method, the concentration of the coenzyme-A (CoA-SH), which is produced when HMG-CoA is reduced to a mevalonate salt by the action of HMG-CoA reductase, is determined by spectroscopy and the activity of HMG-CoA reductase is calculated therefrom.

3 g of liver tissue taken from each sacrificed rat of Step 2 was washed successively with 100 ml of a cold Saline (0.15M NaCl) and 100 ml of a cold buffer solution A (0.1M triethanolamine, HCl/0.2M EDTA/2 mM dithiothreitol). The cold buffer solution A was added to the liver tissue in an amount of 2 ml per 1 g of the liver tissue and the mixture was homogenized with a homogenizer. The homogenate was centrifuged (15,000×g for 15 minutes), and then, the supernatant was ultracentrifuged (100,000×g for 60 minutes) to obtain microsomal precipitates. The precipitates thus obtained were washed with 2 mL of a cold buffer solution A and ultracentrifuged (100,000×g for 60 minutes) to obtain precipitates. The precipitates thus obtained were washed with a 1 mL of cold buffer solution A and kept in a 1.5 mL tube at −70° C.

The reaction substrates used in the measurement of HMG-CoA reductase activity were as follows:
 i) buffer solution B: 0.1M triethanolamine, HCl/0.02M EDTA (pH7.4),
 ii) HMG-CoA solution: 150 mmoles/culture medium, and
 iii) NADPH solution: 2 mmoles/culture medium.

The suspension (microsome) prepared in the above was mixed with the reaction substrate and the resulting mixture was placed in a centrifugation tube and reacted at 37° C. for 30 minutes. The reaction mixture was treated with 20 μl of 0.1M sodium arsenite and allowed to stand for 1 minute. Then, the mixture was reacted with 100 μl of citrate buffer solution (2M citrate/3% sodium tungstate, pH 3.5) at 37° C. for 10 minutes followed by centrifugation (25,000×g for 15 minutes) to remove protein. 1 mL of the supernatant thus obtained was transferred into a tube with a cap and 0.2 mL of 2M tris-HCl solution (pH 10.6) and 0.1 ml of 2M tris-HCl solution (pH 8.0) were added thereto to adjust the pH of the reaction to 8.0. Then, the reaction was mixed with 20 μl of DTNB buffer solution (3mM DTNB/0.1M triethanolamine/ 0.2M EDTA, pH 7.4) and the absorbance of the mixture was determined at 412 nm to calculate the amount of CoA-SH (activity of HMG-COA reductase). The inhibition of HMG-CoA reductase activity of the control and treated groups were calculated based on the above results. The results are shown in Table X.

TABLE X

| Dietary group | Control group | Lovastatin group | BN30063 group | BN30064 group | BN30067 group |
|---|---|---|---|---|---|
| HMG-CoA reductase | 245.41 ± 12.01 | 173.25 ± 12.86 | 196.11 ± 15.47 | 124.74 ± 17.09 | 136.15 ± 11.71 |
| Inhibition of HMG-CoA reductase activity (%) | 0 | 29.40 | 20.09 | 49.17 | 44.52 |

As can be seen in Table X, the HMG-CoA reductase activities observed in the BN30063, BN30064 and BN30067 groups are lower than that of the control group by 20 to 49%.

Experimental Example 7

Inhibitory Effect of Phenolic Acid Derivatives (BN30063, BN30064, BN30067) on Hyperlipemia in Rabbit Step 1: Administration of Lovastatin and Phenolic Acid Derivatives (BN30063, BN30064, BN30067) to Rabbits Healthy male New Zealand White rabbits, each weighing about 2.0 to 2.3 kg, were supplied from Yeonam Horticulture and Animal Husbandry College (Korea) and raised under a breeding environment of temperature 20±2° C., relative humidity 55±10%, and photoperiod 12L/12D. The rabbits were divided into 5 groups, which were fed with 5 different diets, i.e., the control group fed with RC4 diet (Oriental Yeast Co., Japan) comprising moisture (7.6%), crude protein (22.8%), crude fat (2.8%), crude ash (8.8%), crude cellulose (14.4%) and soluble nitrogen-free substances (43.7%) plus cholesterol (1%) and four treatment groups further fed with lovastatin or BN30063, BN30064, BN30067 in addition to the feed of the control group. The rabbits were fed for 8 weeks while being allowed free access to the diets and water. The feed compositions and experiment regimens of the test groups are shown in Table XI.

TABLE XI

| Test group | Number of rabbit | Duration of administration | Dietary |
|---|---|---|---|
| Control group | 10 | 8 weeks | 1% cholesterol + RC4 diet |
| Lovastatin group | 10 | 8 weeks | 1% cholesterol + lovastatin (0.003 wt %) + RC4 diet |
| BN30063 group | 10 | 8 weeks | 1% cholesterol + BN30063 (0.025 wt %) + RC4 diet |
| BN30064 group | 10 | 8 weeks | 1% cholesterol + BN30064 (0.025 wt %) + RC4 diet |
| BN30067 group | 10 | 8 weeks | 1% cholesterol + BN30067 (0.025 wt %) + RC4 diet |

Step 2: Analysis for Fatty Streak in the Main Artery

The rabbits raised in Step 1 were sacrificed and their chests were incised. The incision was performed downward to the diaphragm along the aortic arch and the fat surrounding the main artery was removed. The main artery was incised in the middle along the longitudinal axis from the second aortic intercostal artery anastomoses to the seventh aortic intercostal artery anastomoses and fixed with 10% neutral buffered formalin for 24 hours. Then, the incised main artery was pinned to a dish for staining of fatty streaks according to the method of Esper, E., et al. {J. Lab. Clin. Med., 121, 103-110 (1993)}. The artery was washed with propylene glycol three times for 2 minutes respectively. The artery was stained for 30 minutes with a saturated solution of Oil Red O (ORO, Sigma Co.) dissolved in propylene glycol. Thereafter, the artery was washed with 85% propylene glycol twice for 3 minutes respectively to remove the remaining staining solution and, then the artery was washed with physiological saline once. The artery was photographed and the photograph was traced. The proportion (%) of stained region (fatty streak region) per unit area of the artery was determined with an image analyzer (LEICA, Q-600, Germany). The significant differences between the test groups were tested by student t-test using Microsoft excel (version 7.0) program As a result, it was shown that the proportions of the fatty streak region in the test groups treated with lovastatin and phenolic acid derivatives (BN30063, BN30064, BN30067) were significantly lower than that of the control group and BN30064 inhibited the fatty streak comparable to lovastatin. Considering that the administration concentration of BN30064 was lower than that of lovastatin, it was noted that BN30064 has effect of preventing arteriosclerosis (Table XII).

TABLE XII

| Control group | Lovastatin group | BN30063 group | BN30064 group | BN30067 group |
|---|---|---|---|---|
| 54.0 ± 79[a] (n = 10) | 30.3 ± 12[b] (n = 10) | 44.8 ± 10.5 (n = 10) | 31.2 ± 11.6[b] (n = 10) | 43.0 ± 13.9[b] (n = 10) |

[a]data are expressed as 'average ± standard deviation'
[b]showing statically significant difference from the control group (T-test, $p < 0.05$)

Step 3: Chemical Analysis of Blood

Blood samples taken from the rabbits treated with phenolic acid derivatives (BN30063, BN30064, BN30067) were subjected to a chemical analysis of blood. As a result, the blood samples of the BN30064 group showed a significantly low of total cholesterol ($p<0.05$) and all the samples of other treated groups showed total cholesterol levels lower than that of the control group. For HDL, the control group showed the lowest value while the BN30064 group showed a significantly increased value (p<0.05) and other groups also total cholesterol levels higher than that of the control group.

Further, GOT and GPT, which are associated with hepatotoxicosis, showed similar levels in the control group and BN30063, BN30064 and BN30067 groups. However, lovastatin showed highest GOT and GPT values among the test groups, like in the experiment of food compositions, which indicates that it has toxicity to the liver (Table XIII).

TABLE XIII

| | TC (mg/dl) | HDL (mg/dl) | GOT (IU/L) | GPT (IU/L) |
|---|---|---|---|---|
| Control group | 1808 ± 54[a] | 69 ± 13 | 54 ± 13 | 30 ± 19 |
| Lovastatin group (1 mg/kg, n = 10) | 1739 ± 86 | 70 ± 6 | 105 ± 47[b] | 47 ± 18 |
| 0.025% BN30063 group (n = 10) | 1643 ± 194 | 81 ± 16 | 44 ± 19 | 27 ± 12 |
| 0.025% BN30064 group (n = 10) | 1596 ± 191[b] | 85 ± 15 | 58 ± 17 | 34 ± 16 |
| 0.025% BN30067 group (n = 10) | 1710 ± 251 | 81 ± 14 | 62 ± 17 | 33 ± 12 |

[a]data are expressed as 'average ± standard deviation'
[b]showing statically significant difference from the control group (T-test, $p < 0.05$)

Step 4: Morphological Observation of Liver Tissue

Proportions of cells in the liver acinus containing excessive fat or modified to have irregular arrangement due to a high cholesterol diet were classified into four grades, from 1+ to 4+. There was not observed any abnormality in the liver tissue of the test groups treated with the phenolic acid derivatives (BN30063, BN30064, BN30067), while the lovastatin group showed a grade higher than that of the control group, which indicates sever lesion in the liver cells (Table XIV).

TABLE XIV

| Control group | Lovastatin group | BN30063 group | BN30064 group | BN30067 group |
|---|---|---|---|---|
| 3.79 ± 0.7[a] (n = 10) | 3.83 ± 0.5[b] (n = 10) | 3.71 ± 0.35 (n = 10) | 3.70 ± 0.10 (n = 10) | 3.82 ± 0.8 (n = 10) |

[a]numerical value obtained by classifying into 1+ (0–25%), 2+ (26–50%), 3+ (51–75), 4+ (76–100%) according to the abnormal fat content in the liver acinus, expressed as 'average ± standard deviation'

Step 5: Histological Observation of the Organs

Tissues of the lung, myocardium, kidney and muscle taken from the rabbits treated with the phenolic acid derivatives (BN30063, BN30064, BN30067) were visually examined for pathological changes using a microscope. Throughout the test groups, no pathogenic abnormality was found. There was found no evidence indicating that the test substances used in this experiment has toxicity to organs and muscle.

Formulation 1: Preparation of Hard Capsule as Pharmaceutical Formulation

Hard capsules were prepared using the following ingredients:

| | Quantity (mg/capsule) |
|---|---|
| Active ingredient (BN30028) | 20 |
| Dry starch | 160 |
| Magnessium stearate | 20 |
| Total | 200 mg |

The above ingredients were mixed thoroughly and filled in a hard gelatin capsule.

Formulation 2: Foods Containing Phenolic Acid Derivative

Foods containing the phenolic acid derivatives according to the present invention were prepared as follows.

(1) Preparation of Tomato Ketchup and Sauce

A phenolic acid derivatives prepared in Example 1 to Example 11 was added to a tomato ketchup or sauce in an amount ranging from 0.2 wt % to obtain a health-improving tomato ketchup or sauce.

(2) Preparation of Foods Containing Wheat Flour

A phenolic acid derivatives prepared in Example 1 to Example 1I was added to wheat flour in an amount ranging from 0.5 wt % and breads, cakes, cookies, crackers and noodles were prepared by using the mixture to obtain health-improving foods.

(3) Preparation of Soups and Gravies

A phenolic acid derivatives prepared in Example 1 to Example 11 was added to soups and gravies in an amount ranging from 0.1 wt % to obtain health-improving soups and gravies.

(4) Preparation of Ground Beef

A phenolic acid derivatives prepared in Example 1 to Example 11 was added to ground beef in an amount ranging from 10 wt % to obtain health-improving ground beef.

(5) Preparation of Dairy Products

A phenolic acid derivatives prepared in Example 1 to Example 11 was added to milk in an amount ranging from 5 wt % to obtain health-improving milk, and various dairy products such as butter and ice cream were prepared therefrom.

In case of a cheese preparation, a phenolic acid derivative was added to coagulated milk protein and, in case of a yogurt preparation, a phenolic acid derivative was added to coagulated milk protein obtained after the fermentation.

Formulation 3: Beverages Containing Phenolic Acid Derivative (1) Preparation of Vegetable Juice A phenolic acid derivatives prepared in Example 1 to Example 11 was added to 1000 mL of tomato or carrot juice in an amount of 5 g to obtain a health-improving vegetable juice.

(2) Preparation of Fruit Juice

A phenolic acid derivatives prepared in Example 1 to Example 11 was added to 1000 mL of apple or grape juice in an amount of 1 g to obtain a health-improving fruit juice.

INDUSTRIAL APPLICABILITY

As described through the above examples, the phenolic acid derivatives according to the present invention and the composition for prevention and treatment of blood lipid-related diseases comprising the phenolic acid derivatives can lower blood lipid level and inhibit cholesterol metabolism-related enzymes but do not have toxicity, thereby having excellent effects of preventing and treating blood lipid-related diseases. Therefore, they can be useful in the medical product and health food industries.

What is claimed is:

1. A compound of chemical formula I:

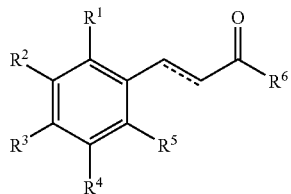

wherein,
each of $R^1$, $R^2$, $R^3$, $R^4$, and $R^5$, independently, are hydroxy or $C_1$-$C_6$ alkoxy;
$R^6$ is

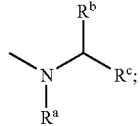

$R^a$ is hydrogen or acetyl;
$R^b$ is $COOR^d$;
$R^c$ is $C_1$-$C_6$ alkyl substituted with $COOR^d$; and
$R^d$ is hydrogen, methyl, or benzyl.

2. A compound of 2-[3-(4-hydroxyphenyl)propionylamino] pentanedioic acid diethyl ester.

3. A composition for treating a blood lipid level-related disease selected from the group consisting of hyperlipidemia, hypercholesterolemia, arteriosclerosis and fatty liver, comprising an effective amount of the compound of claim 1.

4. A foodstuff for treating hyperlipidemia, hypercholesterolemia, arteriosclerosis, or fatty liver, comprising an effective amount of the compound of claim 1.

5. A method of treating a blood lipid level-related disease selected from the group consisting of hyperlipidemia, hypercholesterolemia, arteriosclerosis and fatty liver, comprising administering a therapeutically effective amount of the compound of claim 1.

6. A method of treating a blood lipid level-related disease selected from the group consisting of hyperlipidemia, hypercholesterolemia, arteriosclerosis and fatty liver, comprising administering a therapeutically effective of the compound of claim 2.

* * * * *